United States Patent [19]

Friary et al.

[11] Patent Number: 5,665,735
[45] Date of Patent: Sep. 9, 1997

[54] UNBRIDGED BIS-ARYL CARBINOL DERIVATIVES COMPOSITIONS AND METHODS OF USE

[75] Inventors: Richard Friary, Bridgewater; John J. Piwinski, Parsippany; Jesse K. Wong, Union, all of N.J.

[73] Assignee: Schering Corporation, Kenilworth, N.J.

[21] Appl. No.: 459,149

[22] Filed: Jun. 2, 1995

Related U.S. Application Data

[63] Continuation of Ser. No. 307,801, filed as PCT/US93/02289, Mar. 22, 1993, which is a continuation-in-part of Ser. No. 858,919, Mar. 27, 1992, abandoned.

[51] Int. Cl.⁶ .................. A61K 31/445; C07D 211/22; C07D 211/26; C07D 211/32
[52] U.S. Cl. .................. 514/318; 546/193; 546/194
[58] Field of Search .................. 546/193, 194; 514/318

[56] References Cited

U.S. PATENT DOCUMENTS

| | | | |
|---|---|---|---|
| 2,739,968 | 3/1956 | Sperrer et al. | 546/194 |
| 2,898,339 | 8/1959 | Wheeler et al. | 546/194 |
| 3,325,501 | 6/1967 | Ettinsen | 546/80 |
| 3,326,924 | 6/1967 | Villani | 546/93 |
| 3,717,647 | 2/1973 | Villani | 546/315 |
| 3,803,153 | 4/1974 | Villani | 546/89 |
| 3,803,154 | 4/1974 | Drukker | 540/587 |
| 3,922,276 | 11/1975 | Duncan, Jr. et al. | 546/226 |
| 3,956,296 | 5/1976 | Duncan, Jr. et al. | 544/730 |
| 3,966,944 | 6/1976 | Carter | 514/318 |
| 4,032,642 | 6/1977 | Duncan, Jr. et al. | 514/237.2 |
| 4,105,849 | 8/1978 | Hamilton et al. | 544/129 |
| 4,282,233 | 8/1981 | Villani | 514/290 |
| 4,355,036 | 10/1982 | Villani | 514/316 |
| 4,540,780 | 9/1985 | Downs | 544/129 |
| 4,609,664 | 9/1986 | Hasspacher | 514/324 |
| 4,628,095 | 12/1986 | Rorig et al. | 546/234 |
| 4,632,925 | 12/1986 | Mullin et al. | 514/256 |
| 4,659,716 | 4/1987 | Villani et la. | 514/290 |
| 4,797,489 | 1/1989 | Abou-Gharbia et al. | 544/331 |
| 4,826,853 | 5/1989 | Piwinski et al. | 514/253 |
| 4,835,157 | 5/1989 | Press et al. | 544/258 |
| 5,089,496 | 2/1992 | Piwinski et al. | 514/253 |
| 5,151,423 | 9/1992 | Piwinski et al. | 514/254 |
| 5,166,205 | 11/1992 | Cuberes-Altisent et al. | 514/252 |
| 5,432,175 | 7/1995 | Piwinski | 514/252 |

FOREIGN PATENT DOCUMENTS

| | | |
|---|---|---|
| 638971 | 4/1964 | Belgium . |
| 644121 | 8/1964 | Belgium . |
| 0042544 | 12/1981 | European Pat. Off. . |
| 818103376 | 3/1982 | European Pat. Off. . |
| 0235463 | 9/1987 | European Pat. Off. . |
| 0283310 | 9/1988 | European Pat. Off. . |
| 0371805 | 6/1990 | European Pat. Off. . |
| 0385350 | 9/1990 | European Pat. Off. . |
| 17764 | 4/1964 | Ireland . |
| 8803138 | 5/1988 | WIPO . |
| 8910369 | 11/1989 | WIPO . |
| 9110647 | 7/1991 | WIPO . |
| 9206971 | 4/1992 | WIPO . |

OTHER PUBLICATIONS

Villani et al., Journal of Medicinal Chemistry, vol. 15, No. 7, pp. 750–754 (1972).
Arzn. Forsh 36 1311–1314 (1986).

(List continued on next page.)

*Primary Examiner*—C. Warren Ivy
*Assistant Examiner*—D. Margaret M. Mach
*Attorney, Agent, or Firm*—Henry C. Jeanette

[57] ABSTRACT

Disclosed is a compound of Formula 1.0:

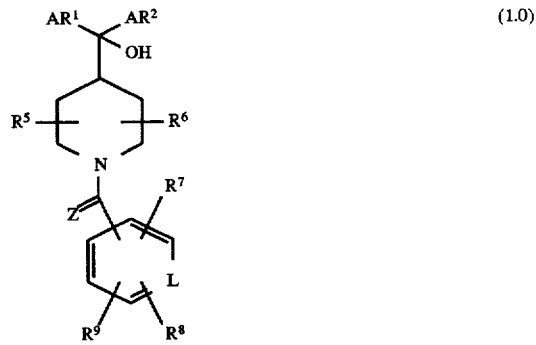

or a pharmaceutically acceptable salt or solvate thereof, wherein:

$AR^1$ represents

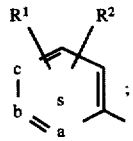

$AR^2$ represents

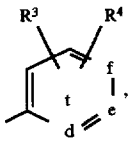

or a five-membered heterocyclic aromatic group selected from the group consisting of Formulas I to XII, wherein the substitutable carbon atoms of the five-membered heterocyclic group can optionally be substituted with a group $R^1$.

Also disclosed are pharmaceutical compositions containing compounds of Formula 1.0.

Further disclosed is a method for treating asthma, allergy and inflammation by administering an anti-asthmatic, anti-allergic or anti-inflammatory, respectively, effective amount of a compound of Formula 1.0.

22 Claims, No Drawings

OTHER PUBLICATIONS

Galantay et al., Journal of Medicinal Chemistry, vol. 17, No. 12, pp. 1316 to 1327 (1974).

Ohtaka et al., chem. Pharm. Bull., 35(10) 4124–4129 (1987).

Kennis et al., Drug Development Research, 8:133–140 (1986).

Regnier et al., Eur. J. Med. Chem, 22(1987) 243–250.

Nishikawa et al., J. Med. Chem. 1989, 32, 583–593.

Anagnostopulos, Eur. J. Med. Chem. 24(1989) 227–232.

Ohtaka et al., Chem. Pharm. Bull, 35(8)3270–3275 (1987).

CID et al., Tetrahedron, vol. 44, No. 19, pp. 6197 to 6200 (1988).

Meyer et al., Journal of Medicinal Chemistry, 1989, vol. 32, No. 3, pp. 593–597.

Gubert et al., Azneim–Forsch./Drug Res. 37(II), Nr. 10(1987) pp. 1103–1107.

Bickel, Pharmacological Review, vol. 21, No. 4, pp. 325, and 335–336 (1969).

Wade, Jr., Organic Chemistry, p. 349, Prentice–Hall, Inc. (1987).

UNBRIDGED BIS-ARYL CARBINOL DERIVATIVES COMPOSITIONS AND METHODS OF USE

This is a continuation of application Ser. No. 08/307,801, filed Sep. 26, 1994, which in turn is application No. PCT/US93/02289, filed Mar. 22, 1993, and designating the United States, which PCT Application is in turn a continuation in part of U.S. application Ser. No. 07/858,919, filed to the provisions of 35 U.S.C. §§120,363 and 365 (C).

BACKGROUND OF THE INVENTION

The present invention relates to bis-aryl carbinol derivatives, pharmaceutical compositions and methods of using such derivatives.

European Patent Application Publication Number 0235463, published Sep. 9, 1987 discloses compounds of the formula:

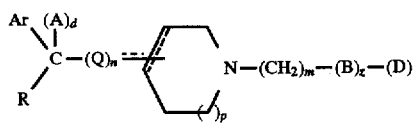

Formula I wherein: Ar, D, and R can be selected from, amongst others, phenyl, substituted phenyl, pyridinyl, thienyl or furanyl; A can be, amongst others, $-O-R^1$ wherein $R^1$ can be, amongst others, hydrogen; Q can be absent because n can be zero; p can be one; m is 0 to 6 and can therefore be one; and B can be absent because z can be zero.

International Publication Number WO 89/10369 discloses compounds of the formula:

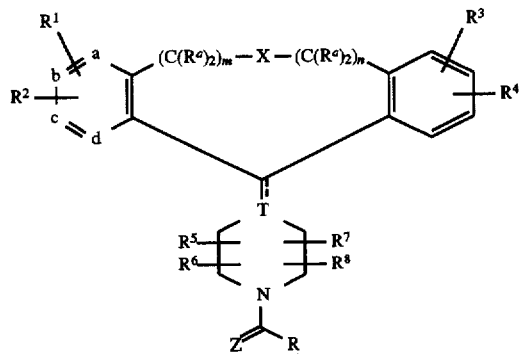

wherein: one of a, b, c and d represents nitrogen or $-NR^{11}-$, wherein $R^{11}$ is, amongst others, $O^-$, and the remaining a, b, c and d groups are CH; T represents carbon or nitrogen, with the dotted line attached to T representing an optional double bond when T is carbon; when m plus n equals 1 or 2, X represents, amongst others, $-O-$ or $-S(O)_e-$ wherein e is 0, 1 or 2; when m plus n represents 0, X can be, amongst others, any substituent for m plus n equalling 1 or a direct bond; when m plus n equals 3 then X equals a direct bond; Z represents $=O$ or $=S$ such that when Z is O, R may be, amongst others,

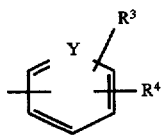

wherein Y is N or $NR^{11}$; when Z represents $=S$, R represents in addition to the R group above, aryloxy or alkoxy.

U.S. Pat. No. 4,826,853 issued to Piwinski et al. on May 2, 1989 is the priority document for WO 88/03138 which published on May 5, 1988. WO 88/03138 discloses compounds of the formula

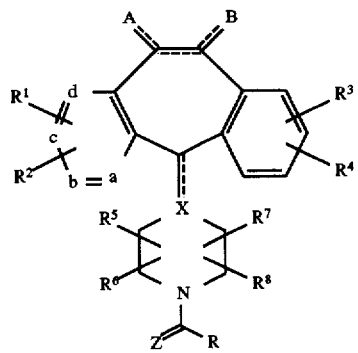

wherein: one of a, b, c and d represents N or $NR^9$ where $R^9$ is, amongst others, O, and the remaining a, b, c and d groups are CH; X represents N or C, which C may contain an optional double bond to carbon atom 11; Z represents O, S or $H_2$ such that when Z is O, R may be, amongst others,

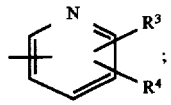

when Z represents S, R represents in addition to the R group above, aryloxy or alkoxy; and when Z represents $H_2$, R can be, amongst others,

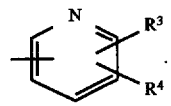

These compounds are disclosed as being useful in the treatment of allergy and inflammation.

In particular, WO88/03138 discloses intermediates having the formulas:

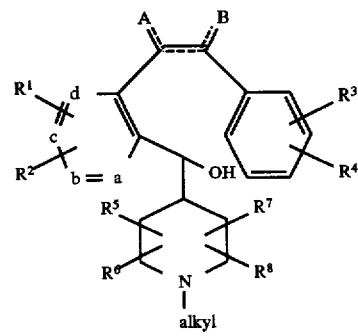

see p. 29;

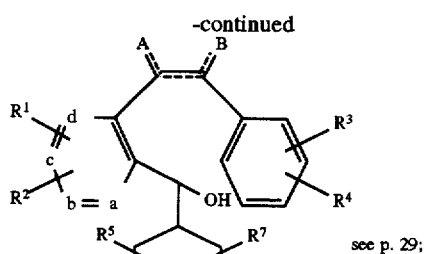

see p. 29;

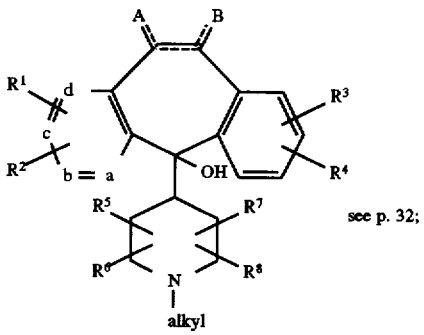

see p. 32;

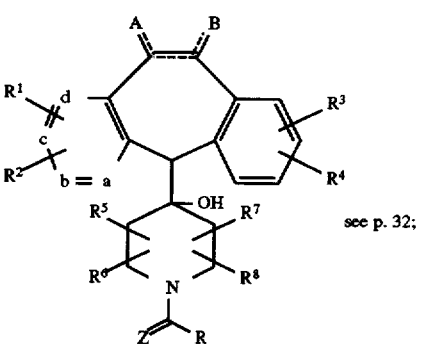

see p. 32;

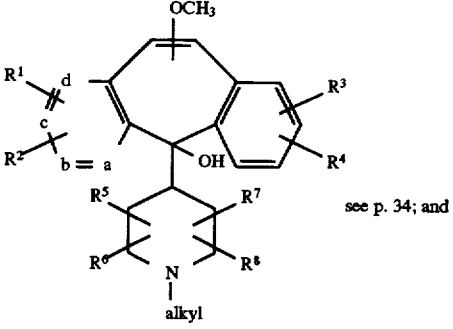

see p. 34; and

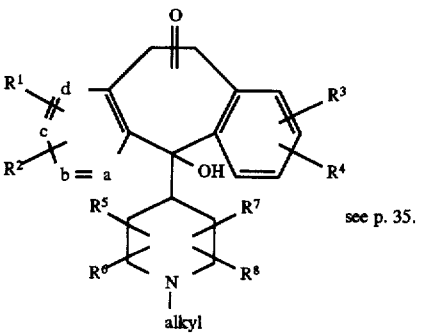

see p. 35.

During the course of research on the compounds disclosed in WO 88/03138, it was generally found that the compounds having a carbonyl group (Z=O) attached to the piperidyl, piperidylidenyl or piperazinyl nitrogen atom were much stronger antagonists of platelet activating factor (PAF) than the compounds having a $CH_2$ group ($Z=H_2$) attached thereto.

WO 90/13548 published on Nov. 15, 1990 on PCT/US90/02251 which was filed on Apr. 30, 1990 and claims priority to U.S. application Ser. No. 345,604 filed May 1, 1989 discloses compounds similar in structure to the compounds disclosed in WO 88/03138 with the difference being that the R group represents an N-oxide heterocyclic group of the formula (i), (ii), (iii), or (iv):

XXVI

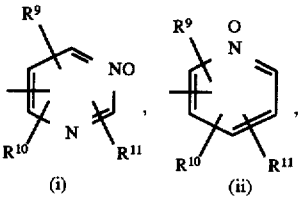

XXVII

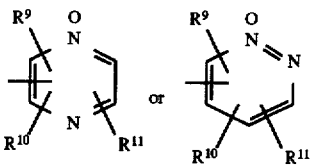

wherein $R^9$, $R^{10}$, and $R^{11}$ can be, amongst other groups, H.

Galantay et al., Journal of Medicinal Chemistry, 1974, Vol. 17, No. 12, pp. 1316 to 1327 discloses oxazole and thiazole analogs of amitripyline. A disclosed intermediate has the formula:

XXXI

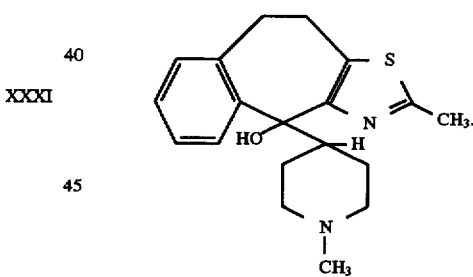

U.S. Pat. No. 4,659,716 discloses an intermediate of the formula:

XXXII

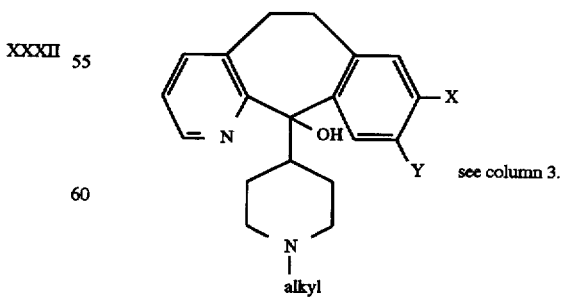

see column 3.

PCT/US89/01689, International Publication Number WO 89/10363, published Nov. 2, 1989, discloses compounds of the formula:

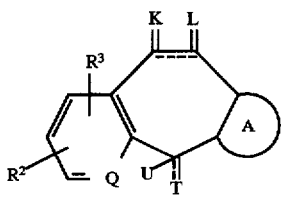

(1.0)

wherein T represents =O or

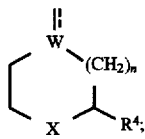

Q represents CH, N or N→O; ring A represents defined heterocyclic aromatic rings (see pp. 3 and 4 for example), U is —H or —OH when the bond between W and the cyclohepta ring is a single bond; W represents C, N or N→O and the dotted line drawn to W from the cyclohepta ring represents an optional double bond when W is C, or is absent when W is N→O; and X can be, amongst others:

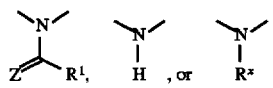

wherein Z is O or S; $R^1$ can be, amongst others, H, alkyl, cycloalkyl, aryl, and heteroaryl (the definition of heteroatom includes N→O); and $R^x$ can be alkyl, aralkyl or aryl.

SUMMARY OF THE INVENTION

We have now unexpectedly found that compounds having a carbon atom to which the following groups are attached: (a) a —OH group; (b) two aryl groups, or two heteroaryl groups, or one aryl and one heteroaryl group, or one aryl and one five membered heterocyclic aromatic group, or one heteroaryl and one five membered heterocyclic aromatic group; and (c) a 4-piperidyl group having a pyridine N-oxide group bound to the piperidine nitrogen through a C=Z group; in which the groups listed in (b) are not bridged to form a tricyclic ring system, provide good activity as PAF antagonists, and surprisingly have a longer duration of activity than other known compounds.

In particular, we have discovered such characteristics in compounds represented by Formula 1.0:

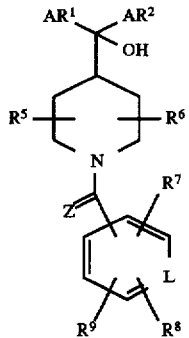

(1.0)

or a pharmaceutically acceptable salt or solvate thereof, wherein:

$AR^1$ (or $Ar^1$) represents

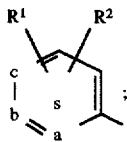

$AR^2$ (or $Ar^2$) represents

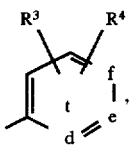

or a five-membered heterocyclic aromatic group selected from the group consisting of Formulas I to XII:

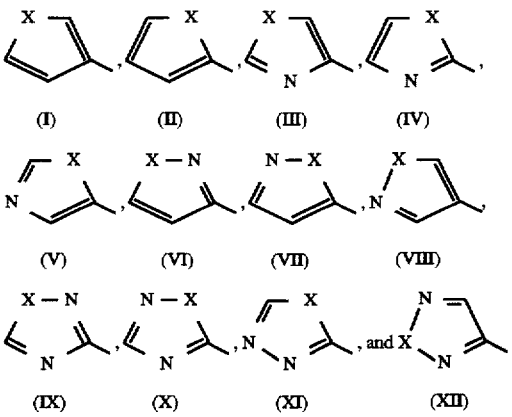

wherein X represents O, S, or $NR^{10}$ wherein $R^{10}$ is as defined below, said five-membered heterocyclic aromatic group can optionally be substituted with a group $R^1$ as defined below;

one of a, b and c represents N or $N^+O^-$ and the remaining others (i.e., the remaining a, b, and c) represent C (carbon), or all of a, b and c represent C;

one of d, e and f represents N or $N^+O^-$ and the remaining others (i.e., the remaining d, e, and f) represent C, or all of d, e and f represents C.

L represents N or $N^+O^-$;

$R^{12}$, $R^2$, $R^3$, and $R^4$ are each independently selected from the group consisting of: H, halo, —$CF_3$, —$OR^{11}$, —$C(O)R^{11}$, $SR^{11}$, —$S(O)_qR^{12}$ wherein q is 1 or 2, —$N(R^{11})_2$, —$NO_2$, —$OC(O)R^{11}$, —$CO_2R^{11}$, —$OCO_2R^{12}$, —$CON(R^{11})_2$, —$NR^{11}C(=O)R^{11}$, —CN, alkyl, aryl, alkenyl and alkynyl, said alkyl group is optionally substituted with —$OR^{11}$, —$SR^{11}$, —$N(R^{11})_2$ or —$CO_2R^{11}$, and said alkenyl group is optionally substituted with halo, —$OR^{12}$ or —$CO_2R^{11}$;

adjacent $R^1$ and $R^2$ groups can optionally be taken together to form a benzene ring fused to the ring s;

adjacent $R^3$ and $R^4$ groups can optionally be taken together to form a benzene ring fused to the ring t;

$R^5$ and $R^6$ are each independently selected from the group consisting of: H, alkyl and aryl; or $R^5$ can be taken together with $R^6$ to represent =O or =S;

$R^7$, $R^8$ and $R^9$ are each independently selected from the group consisting of: H, halo, —$CF_3$, —$OR^{11}$, —C(O)

R$^{11}$, —SR$^{11}$, —S(O)$_e$R$^{12}$ wherein e is 1 or 2, —N(R$^{11}$)$_2$, —NO$_2$, CN, —CO$_2$R$^{11}$, —OCO$_2$R$^{12}$, —OC(O)R$^{11}$, —CON(R$^{11}$)$_2$, —NR$^{11}$C(O)R$^{11}$, alkyl, aryl, alkenyl and alkynyl, —CO$_2$R$^{11}$, and said alkenyl group is optionally substituted with halo, —OR$^{12}$ or —CO$_2$R$^{11}$;

R$^{10}$ is selected from the group consisting of: H and alkyl;

R$^{11}$ is selected from the group consisting of: H, alkyl and aryl;

R$^{12}$ is selected from the group consisting of: alkyl and aryl; and

Z is selected from the group consisting of: O and S, or Z optionally represents H and R$^{10}$.

Preferrably, the five membered heterocyclic ring is selected from the group consisting of:

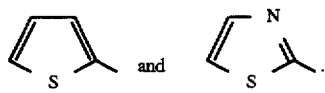

In preferred compounds of Formula 1.0, b and c of AR$^1$ are C and a can be C or N; e and f of AR$^2$ are carbon and d can be C or N, or AR$^2$ can be a 5-membered ring selected from the group consisting of Formulas I to V, IX, and X; AR$^1$ and AR$^2$ are each independently selected from the group consisting of: phenyl, halophenyl, thienyl, thiazolyl, and pyridyl, most preferred are the AR$^1$ and AR$^2$ combinations of: phenyl and phenyl, pyridyl and pyridyl, pyridyl and phenyl, thienyl and phenyl, thiazolyl and phenyl, thiazolyl and pyridyl, pyridyl and chlorophenyl, chlorophenyl and chlorophenyl, thienyl and chlorophenyl, and thiazolyl and chlorophenyl; R$^1$, R$^2$, R$^3$, and R$^4$ are each independently selected from the group consisting of: H, halo, —OR$^1$, and alkyl, with H or halo being most preferred and H and Cl being even still more preferred; R$^5$ and R$^6$ are each independently selected from the group consisting of: H and alkyl, with H being most preferred; R$^7$, R$^8$, and R$^9$ are each independently selected from the group consisting of: H, halo, —OR$^{11}$, and alkyl, with H being most preferred; Z is selected from the group consisting of O, and H and R$^{10}$ wherein R$^{10}$ is preferably H, with Z being most preferably O; and L is N$^+$O$^-$.

Even more preferred compounds of this invention are represented by Formula 1.0A:

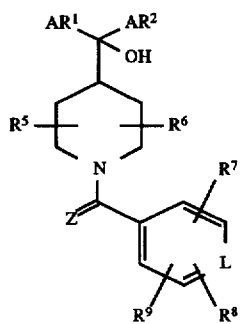

(1.0A)

wherein the substituents are as defined above for Formula 1.0A.

Still more preferred compounds are-those of Formula 1.0A wherein: b and c of AR$^1$ are C and a can be C or N; e and f of AR$^2$ are carbon and d can be C or N; AR$^1$ and AR$^2$ are each independently selected from the group consisting of: phenyl, halophenyl, thienyl, thiazolyl, and pyridyl, most preferred are the AR$^1$ and AR$^2$ combinations of phenyl and phenyl, pyridyl and pyridyl, pyridyl and phenyl, thienyl and phenyl, thiazolyl and phenyl, thiazolyl and pyridyl, pyridyl and chlorophenyl, chlorophenyl and chlorophenyl, thienyl and chlorophenyl, and thiazolyl and chlorophenyl; R$^1$, R$^2$, R$^3$, and R$^4$ are each independently selected from the group consisting of: H; halo, —OR$^{11}$, and alkyl, with H or halo being most preferred and H and Cl being even still more preferred; R$^5$ and R$^6$ are each independently selected from the group consisting of: H and alkyl, with H being most preferred; R$^7$, R$^8$, and R$^9$ are each independently selected from the group consisting of: H, halo, —OR$^{11}$, and alkyl, with H being most preferred; Z is selected from the group consisting of O, and H and R$^{10}$ wherein R$^{10}$ is preferably H, with Z being most preferably O; and L is N$^+$O$^-$.

Representative compounds of this invention include, but are not limited to:

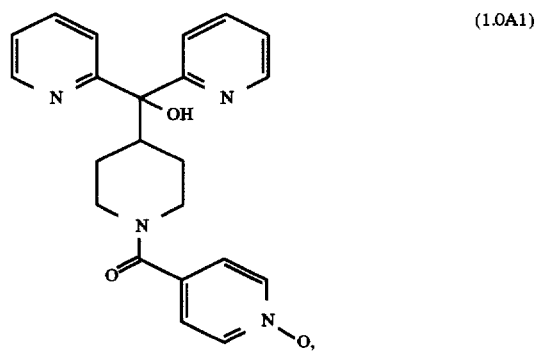

(1.0A1)

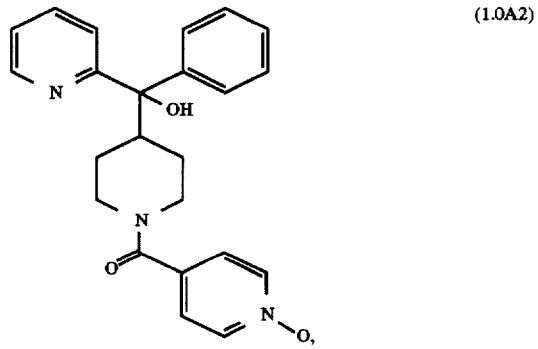

(1.0A2)

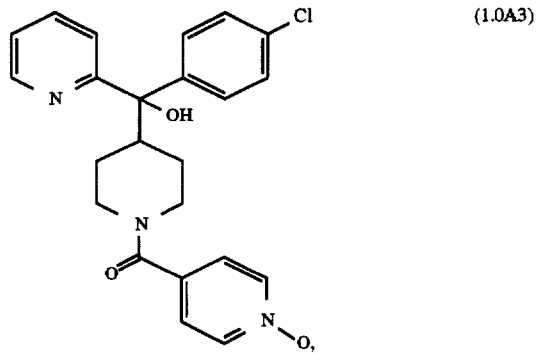

(1.0A3)

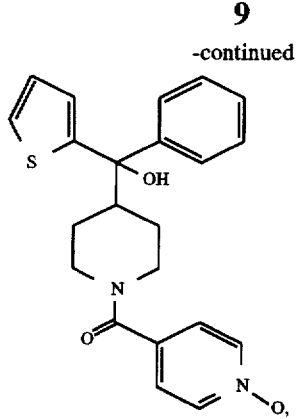 (1.0A4)
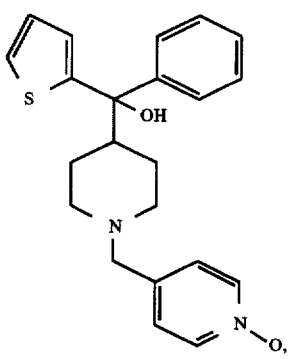 (1.0A5)
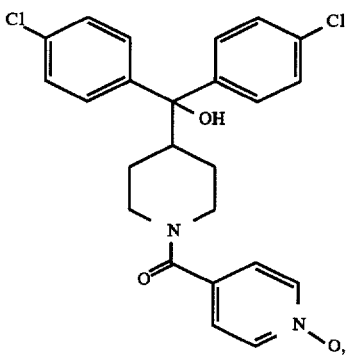 (1.0A6)
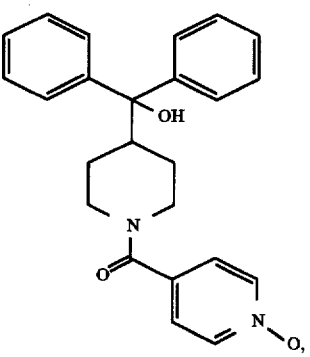 (1.0A7)
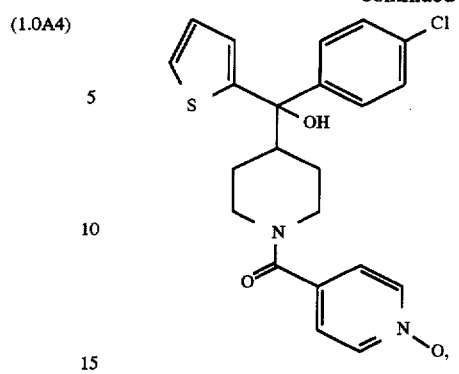 (1.0A8)
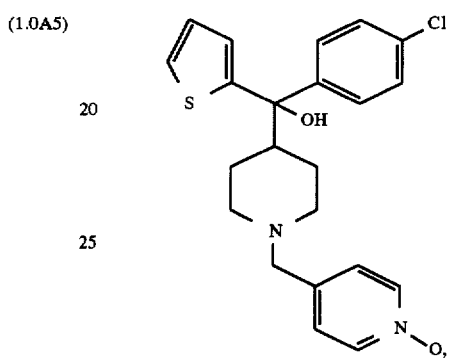 (1.0A9)
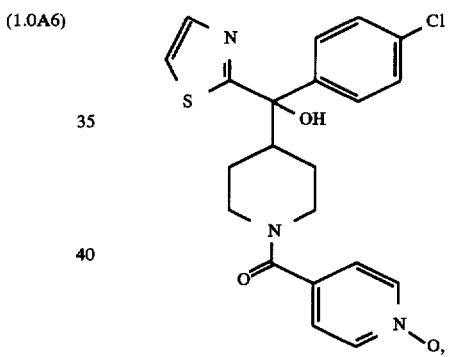 (1.0A10)
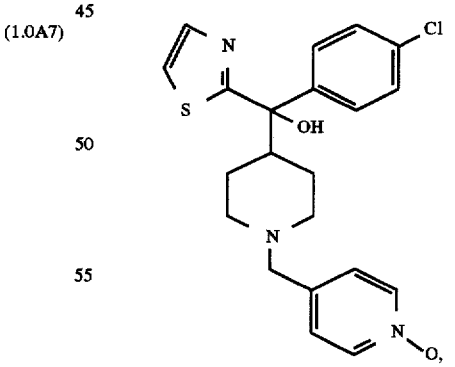 (1.0A11)

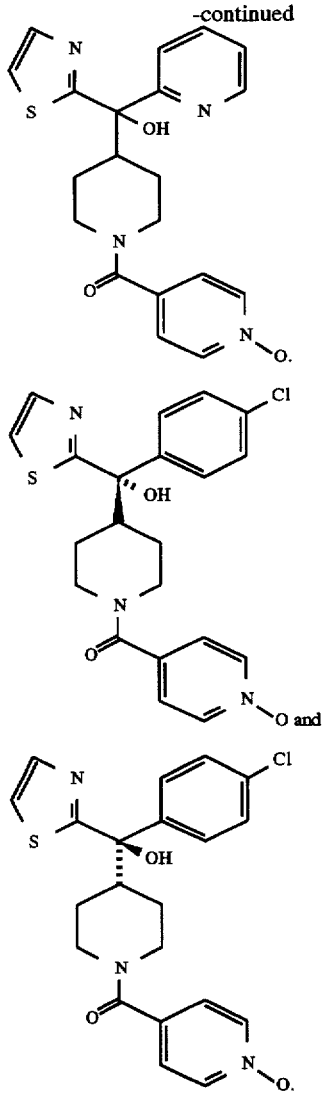

This invention also provides a pharmaceutical composition comprising an effective amount of a compound of Formula 1.0 in combination with a pharmaceutically acceptable carrier.

This invention further provides a method for treating allergy in a mammal comprising administering to the mammal an effective antiallergic amount of a compound of Formula 1.0.

Additionally, this invention provides a method for treating inflammation in a mammal comprising administering to the mammal an effective anti-inflammatory amount of a compound of Formula 1.0.

Further, this invention provides a method for treating asthma in a mammal comprising administering to the mammal an effective anti-asthmatic amount of a compound of Formula 1.0.

DETAILED DESCRIPTION OF THE INVENTION

As used herein, the following terms are used as defined below unless otherwise indicated:

- alkyl—(including the alkyl portions of alkoxy, alkylamino and dialkylamino)—represents straight and branched carbon chains and contains from one to twenty carbon atoms, preferably one to six carbon atoms;

- cycloalkyl—represents saturated carbocyclic rings of from 3 to 20 carbon atoms, preferably 3 to 7 carbon atoms;

- alkenyl—(including the alkenyl portions of alkenyloxy) represents straight and branched carbon chains having at least one carbon to carbon double bond and containing from 2 to 12 carbon atoms, preferably from 3 to 6 carbon atoms;

- alkynyl—(including the alkynyl portions of alknyloxy) represents straight and branched carbon chains having at least one carbon to carbon triple bond and containing from 2 to 12 carbon atoms, preferably from 2 to 6 carbon atoms;

- aryl—represents a carbocyclic group (preferably phenyl or substituted phenyl, including the phenyl portions of phenoxy) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_p$R$^g$ [wherein p is 0, 1 or 2 and R$^g$ is alkyl, phenyl or substituted phenyl], —CF$_3$, amino, alkylamino, dialkylamino, —COOR$^{10}$ or —NO$_2$;

- halo—represents fluoro, chloro, bromo and iodo; and

- substituted phenyl—represents a phenyl group in which 1 to 3 hydrogen atoms thereof are replaced by the same or different substituents independently chosen from halo, alkyl, hydroxy, alkoxy, phenoxy, cyano, cycloalkyl, alkenyloxy, alkynyloxy, —SH, —S(O)$_p$R$^h$ [wherein p is 0, 1 or 2 and R$^h$ is alkyl], —CF$_3$, amino, alkylamino, dialkylamino, —COOR$^{10}$ or —NO$_2$.

Also, unless indicated otherwise, the following abbreviations used herein have the following meanings:

CDI—N,N'-carbonyldiimidazole;
DCC—N,N'-dicyclohexylcarbodiimide;
DEC—1-(3-dimethylaminopropyl)-3-ethylcarbodiimide hydrochloride;
HOBT—1-hydroxybenzotriazole hydrate; and
THF—tetrahydrofuran.

Certain compounds of the invention may exist in different isomeric (e.g., enantiomers and diastereoisomers) as well as conformational forms. The invention contemplates all such isomers both in pure form and in admixture, including racemic mixtures. Enol and tautomeric forms are also included. For example, hydroxy substituted pyridinyl groups can also exists in their keto form:

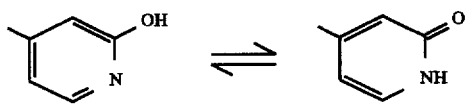

as can certain members of the five-membered heterocyclic groups.

The compounds of the invention of formula 1.0 can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the Ar$^1$ and Ar$^2$ groups of formulas 1.0 and 1.0A can contain one or more substituents R$^1$, R$^2$, R$^3$ and R$^4$ where indicated. In compounds where there is more than one such substituent, each substituent on the ring may be the same or different. Thus, compounds having combinations of such substituents are within the scope of the invention. Also, the lines drawn into the rings from the $R^1$-$R^9$ groups indicate that such groups may be attached at any of the available positions. For example, the $R^1$ and $R^2$ groups may be attached to any carbon atom in $AR^1$ of formula 1.0, while the $R^3$ and $R^4$ groups may be attached to any carbon atom of $AR^2$ of formula 1.0.

$R^5$ and $R^6$ are attached to the piperidyl ring. As such they may be the same or different. The variables $R^5$ and $R^6$ in addition to representing H, may represent variables attached to the same or different carbon atoms in said ring. For example, when $R^5$ and $R^6$ are combined to represent =O or =S, they are attached to the same carbon atom.

The N-oxides are illustrated herein using the terms NO, N→O, N—O and N⁺O⁻. All are considered equivalent as used herein.

Lines drawn into the ring systems indicate that the indicated bond may be attached to any of the substitutable ring carbon atoms.

Certain compounds of the invention will be acidic in nature, e.g. those compounds which possess a carboxyl, phenolic enolic or tautomeric hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The processes A–H below can be employed to produce compounds of Formula 1.0 (i.e., structures 1.1 to 1.6).

A. A compound of Formula 2.0 can be coupled with a compound of Formula 3.0 in the presence of coupling agent such as DEC, DCC or CDI to produce compounds of Formula 1.0 wherein Z is oxygen (i.e., Formula 1.1):

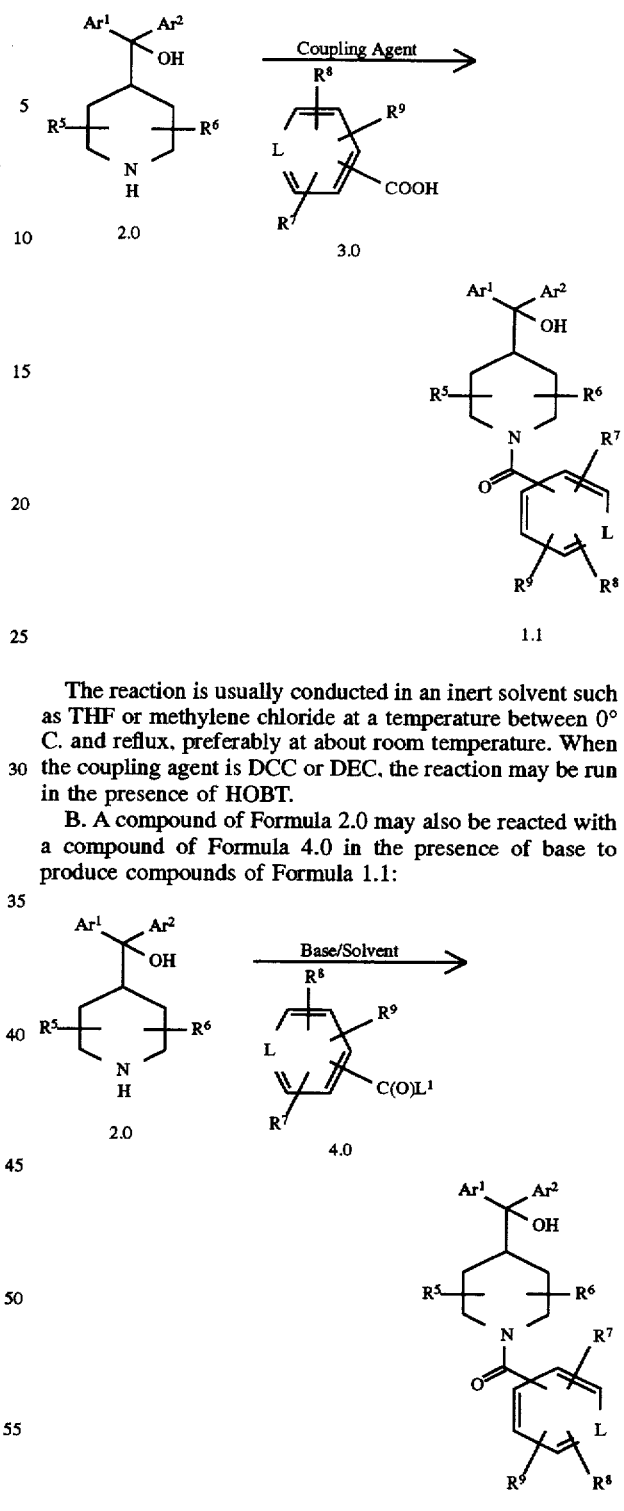

The reaction is usually conducted in an inert solvent such as THF or methylene chloride at a temperature between 0° C. and reflux, preferably at about room temperature. When the coupling agent is DCC or DEC, the reaction may be run in the presence of HOBT.

B. A compound of Formula 2.0 may also be reacted with a compound of Formula 4.0 in the presence of base to produce compounds of Formula 1.1:

Representative examples of suitable bases include pyridine and triethylamine. $L^1$ designates a suitable leaving group. For example, a compound of Formula 4.0 can be an acyl halide (e.g., $L^1$ represents halo) or an acyl anhydride, (e.g., $L^1$ is —O—C(O)—R' wherein R' is alkyl or aryl). Compounds of Formula 4.0 are produced by standard methods known in the art from compounds of Formula 3.0. For example, treatment of a compound of Formula 3.0 with oxalyl chloride in an inert solvent would provide compound 4.0 wherein $L^1$=Cl.

C. Compounds of Formula 1.2 may be prepared directly by reacting the N-alkyl (preferably N-methyl) derivative of Formula 5.0 with a compound of Formula 4.0:

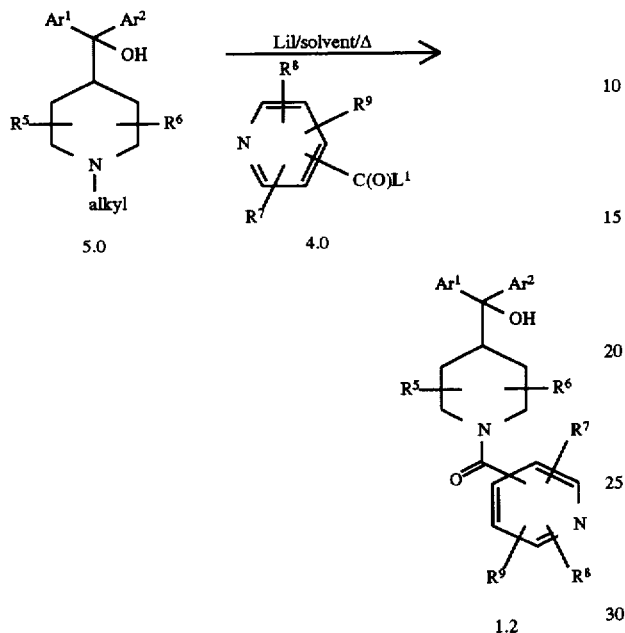

Preferably, the reaction is run in the presence of an appropriate nucleophile (e.g., LiI, and the like) in an inert solvent (e.g., toluene, dioxane or xylenes). $L^1$ is a suitable leaving group such as halo or OC(O)R' where R' is as defined above. A suitable base, can be added, and heating is usually required. Typically, a temperature ranging from about 50° to about 300° C. (preferably about 100° to about 175° C.) is utilized depending on the boiling point of the solvent.

D. A compound of Formula 1.3 may be prepared from a compound of Formula 1.2:

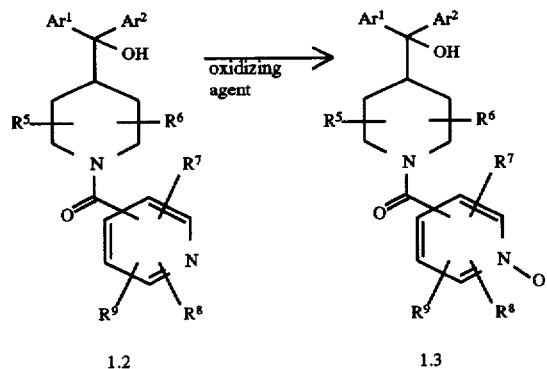

This is accomplished with a suitable oxidizing agent in an inert solvent such as meta-chloroperbenzoic acid (MCPBA) in methylene chloride or hydrogen peroxide in acetic acid. The reaction is usually conducted at a temperature of about −15° C. to reflux. When present, oxidation of other basic amino groups in the molecule (e.g., —$NH_2$, —$N(CH_3)_2$ and the like) can occur with this method; however, in such cases, with excess reagent the N-oxides of Formula 1.3 can be produced. Compounds of Formula 1.2 are prepared as described in methods A to C above.

E. Compounds of Formula 1.4 are best prepared via alkylation of the N–H piperidines of Formula 2.0:

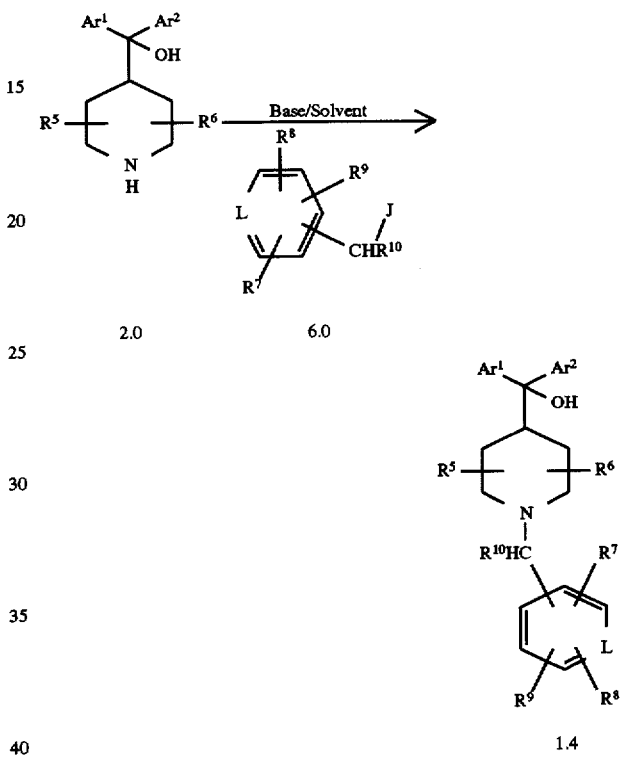

Treatment of 2.0 with the reagent of Formula 6.0, wherein J is a leaving group such as halo, mesyl or tosyl, provides the product of Formula 1.4. The reaction is usually conducted in an inert solvent such as tetrahydrofuran or methylene chloride at a suitable temperature, usually at reflux, although lower temperatures can sometimes be employed. An appropriate base, such as triethylamine or pyridine, is usually present. The base can often be omitted when one of either a, b, c, d, e or f is nitrogen, or one of the R substituents is amino. The appropriately substituted pyridyl reagent of Formula 6.0 can be prepared from the corresponding alcohol using well known procedures (e.g., methanesulfonyl chloride in triethylamine for J=$OSO_2CH_3$ and triphenylphosphine/carbon tetrabromide for J=Br).

F. Alternatively, the compounds of Formula 1.4 may be prepared via reductive amination of the unsubstituted piperidine of Formula 2.0 with the pyridine carboxaldehyde or ketone of Formula 7.0:

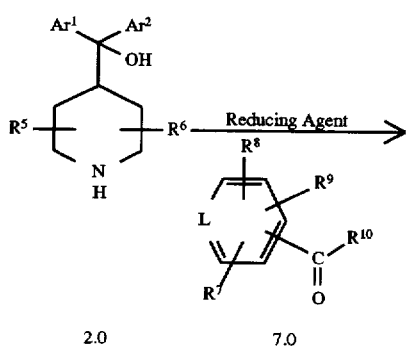

2.0      7.0

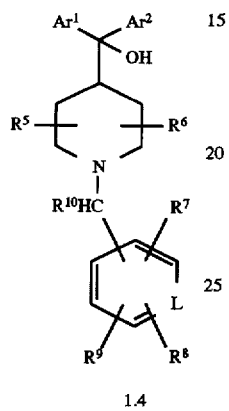

1.4

The reaction is typically carried out in a polar solvent, such as R'OH, (e.g., methanol or ethanol), and optionally in the presence of a water scavenger such as 3 Å molecular sieves. The presence of a reducing agent; such as $NaCNBH_3$ or $H_2/Pd—C$, is necessary for reduction of the intermediate Schiff base. Temperatures for the reaction are typically held between about 0° to about 100° C. depending on the solvent employed and the reactivity of the compound of Formula 7.0. With this method, compounds having less hindered derivatives (i.e., wherein $R^5$, $R^6$ and/or $R^{10}$ are H) may be more easily produced.

G. The compounds of Formula 1.5 may be prepared via reduction of the corresponding amides of Formula 1.1 wherein Z is oxygen:

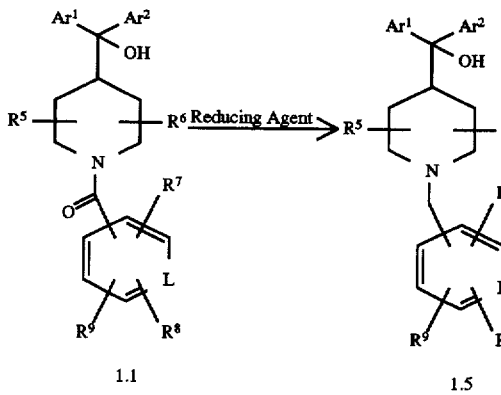

Treatment of the amide of Formula 1.1 with a reducing agent, such as lithium aluminum hydride or similar reducing agent, reduces the carbonyl to provide the compound of Formula 1.5. The reaction is typically carried out in an inert solvent, such as tetrahydrofuran or diethyl ether, at a temperature range of about 0° C. to reflux. This method is limited to cases where the reducing agent will not reduce other functional groups that can be present in the molecule such as esters and ketones. The amide of Formula 1.1 is obtained as discussed above.

H. Compounds of Formula 1.6 are best prepared from the corresponding compounds of Formula 1.1 wherein Z is oxygen (Z=O):

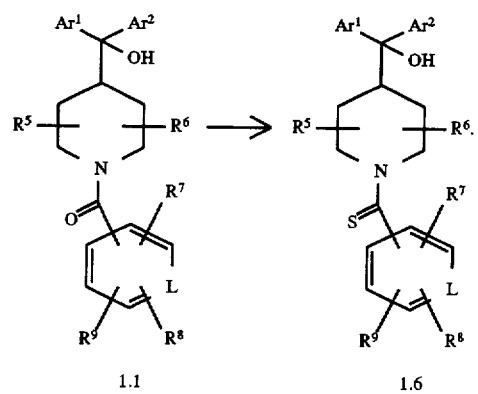

Treatment of a compound of Formula 1.1 with a sulfurating agent such as $P_2S_5$ or Lawesson's reagent may provide a compound of Formula 1.6. The reaction can take place at elevated temperatures ranging from about 50° C. to the reflux temperature of the reaction mixture in pyridine, toluene or other suitable solvents. Lower temperatures can also be employed, e.g., about −5° to about +50° C., depending on the reactivity of the compound.

Compounds of Formula 2.0 are prepared by removal of the carbamoyl moiety (i.e., $CO_2R''$ wherein R'' is alkyl, substituted alkyl (such as $CHClCH_3$ or $CH_2CCl_3$) or aryl) from the corresponding carbamate of Formula 8.0 via either acid (e.g., $HCl/H_2O$/reflux) or base (e.g., $KOH/H_2O$/reflux or alkaline metal carbonates) hydrolysis:

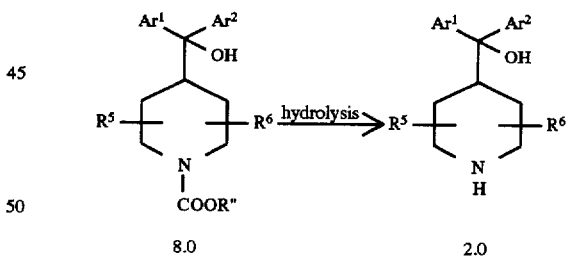

8.0      2.0

Alternatively, depending upon the nature of R'', as determined by one skilled in the art, the compound of Formula 8.0 can be treated with an organometallic reagent (e.g., $CH_3Li$ for $R''=CH_3$), with a reductive reagent (e.g., Zn in acid for $R''=CH_2CCl_3$), with an alcohol or water (e.g., for $R''=CHClCH_3$), or with hydrogen and a noble metal catalyst such as palladium on carbon (e.g., Pd/C and $H_2$ for R''=aralkyl such as benzyl, and the like) to form compounds of Formula 2.0.

The compound of Formula 8.0 (wherein R'' is as defined above) can be prepared from the N-alkyl (preferably N-methyl) compound of Formula 5.0:

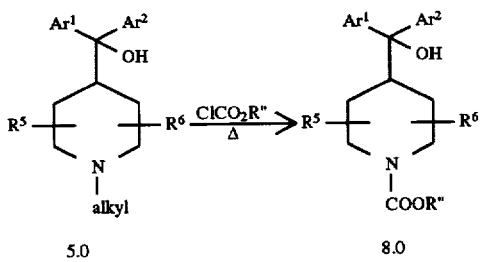

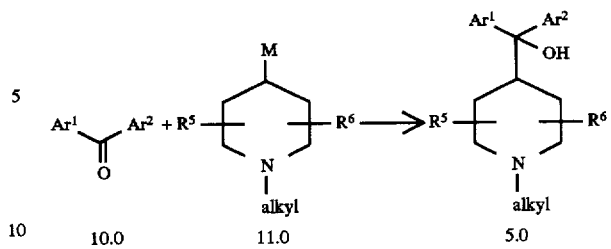

in the manner disclosed in U.S. Pat. Nos. 4,282,233 and 4,335,036 and in WO 88/03138, the disclosures of which are incorporated herein by reference thereto, for similar compounds. For example, the compound of Formula 5.0 can be reacted with the corresponding alkyl chloroformate in an inert solvent, such as toluene, at a suitable temperature, e.g., about 50° to about 100° C. to form a compound of Formula 8.0.

It will also be apparent to one skilled in the art that there are other methods for converting a compound of Formula 5.0 (preferably wherein alkyl is methyl) to a compound of Formula 2.0. For example, treatment of a compound of Formula 5.0 with phosgene followed by aqueous acid produces the unsubstituted piperidine of Formula 2.0. Alternatively, treatment of a compound of Formula 5.0 with BrCN via von Braun reaction conditions would provide the nitrile of Formula 9.0:

The reaction may be refluxed, if necessary to complete it within 1 to 48 hours, after which it is quenched to produce the alcohol of Formula 5.0. The metalated reagent of Formula 11.0 can be prepared via methods well known in the art from the corresponding halo derivative.

Another method for the preparation of compounds of Formula 5.0 involves treatment of the aryl piperidyl ketone of Formula 12.0 or 12.1 with the metalated aryl derivative of Formula 13.0 or 13.1:

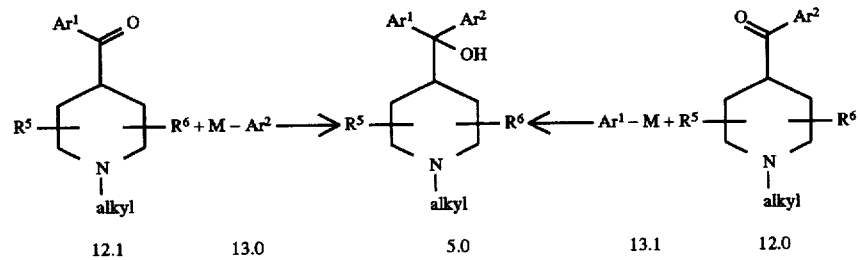

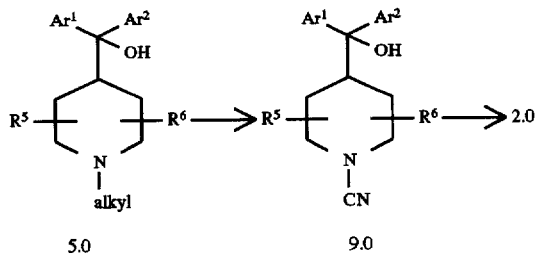

Subsequent hydrolysis of the nitrile of Formula 9.0 under either aqueous basic or acidic conditions will produce a compound of Formula 2.0. This method is preferable when there is substitution on the piperidine ring.

The alcohol of Formula 5.0 can be prepared via the treatment of the ketone of Formula 10.0 with the appropriate metalated reagent of Formula 11.0 (such as a Grignard reagent wherein M=MgX and X is halo) in an inert solvent, such as diethyl ether or tetrahydrofuran:

The reaction is usually conducted in an inert solvent such as tetrahydrofuran or diethyl ether at temperatures ranging from about −78° C. to reflux, but typically at about 0° C. A variety of metalated reagents known in the art can be used in this process, for example, a Grignard reagent wherein M is as defined above.

There are many methods known for the preparation of the various substituted diaryl ketones of Formula 10.0. The choice of which method to use depends largely on the nature of $Ar^1$ and $Ar^2$ and on the substitution in the aryl rings, and such choice is well within the capabilities of those skilled in the art. For example, the compounds of Formula 10.0 can be prepared via a Friedel-Crafts acylation between the acid chloride of Formula 14.0 and the aryl compound of Formula 15.1, or between the acid chloride of Formula 14.1 and the aryl compound of Formula 15.0. The reaction is carried out under usual Friedel-Crafts conditions in an inert solvent and in the presence of a Lewis acid such as aluminum chloride. Alternatively, the reaction can be done under basic conditions wherein the metalated aryl ring compound of Formula 16.0 is treated with the nitride of Formula 17.1, or wherein the compound of Formula 16.1 is treated with the nitrile of Formula 17.0. The reaction is usually conducted in a dry aprotic solvent, such as tetrahydrofuran or diethyl ether, at a variety of temperatures typically ranging from about 0° C. to reflux, depending on the solvent of choice. The resultant imine which is produced from this reaction is simply hydrolyzed in aqueous acid to produce the desired diaryl ketone of Formula 10.0.

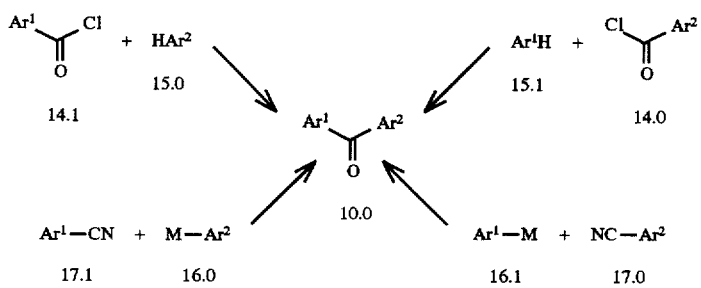

In addition, compounds of Formula 10.0 wherein $Ar^2$ is

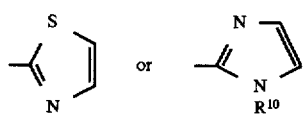

(i.e., compounds of Formulas 10.1 and 10.2) can be prepared by the methods:

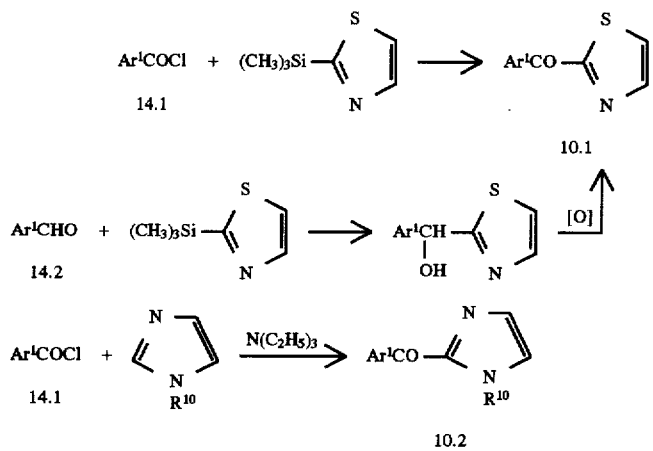

The preparations of compounds of Formulas 10.1 and 10.2, respectively, appear in *J. Org. Chem.* 53, 1748–1761 (1988) and *Ann. Chem.* 145–158. (1988), the disclosure of which is incorporated herein by reference thereto.

There are many methods known for the preparation of the various aryl piperidyl ketones of Formula 12.0 or 12.1. The choice of which method to use depends largely on the nature of $Ar^1$ and Ar2 and on the substitution present in the aryl rings, and such choice is well within the capabilities of those skilled in the art. For example, they can be prepared via a Friedel-Crafts acylation between the acid chloride of Formula. 18.0 with the aryl compound of Formula 15.0 or 15.1. The reaction is done under usual Friedel-Crafts conditions in an inert solvent and in the presence of a Lewis acid such as aluminum chloride. Alternatively, the reaction can be done under basic conditions wherein the metalated aryl compound of Formula 16.0 or 16.1 (such as a Grignard reagent wherein M is as defined above) is treated with the nitrile of Formula 19.0. The reaction is usually conducted in a dry aprotic solvent, such as tetrahydrofuran or diethyl ether, at a variety of temperatures typically ranging from about 0° C. to reflux depending on the solvent of choice. The resultant imine which is produced from this reaction is simply hydrolyzed in aqueous acid to produce the desired aryl piperidyl ketone of Formula 12.0 or 12.1. Conversely, the metalated species and nitrile can be interchanged so that the piperidine is metalated (i.e., Formula 11.0) and the aryl compound is substituted with the nitrile (Formula 17.0 or 17.1). This reaction is conducted under the same conditions as described above to produce the imine which is hydrolyzed to produce the aryl piperidyl ketone of Formula 12.0 or 12.1.

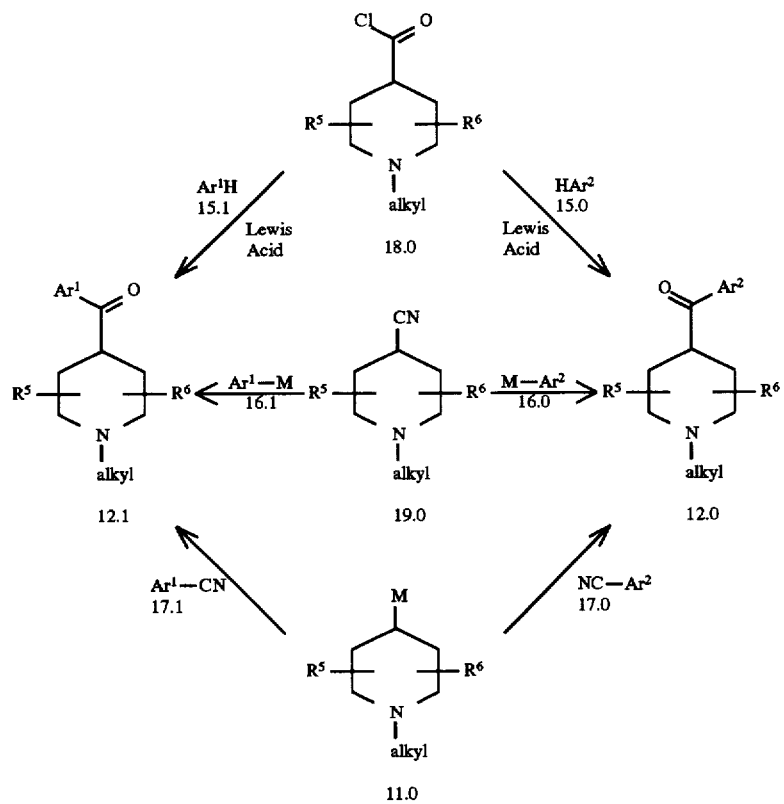

In certain cases some of the processes described above can be shortened by eliminating some of the steps in the sequences. For example, a compound of Formula 8.0 can be prepared directly from the ketone of Formula 10.0 by treating it with sodium in ammonia in the presence of a carbamate of Formula 20.0. The reaction is conducted under standard metal-ammonia conditions in an inert solvent such as tetrahydrofuran. The preparation of these compounds of Formula 8.0 is limited to cases wherein the starting materials lack reactive functionalities that are reactive to sodium (e.g., $R^1$ to $R^4$ are halo).

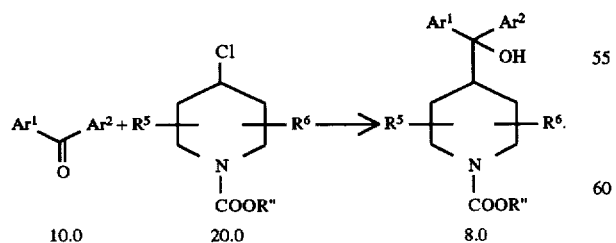

Another route involves the metalation of a substituted pyridine in the C-4 position to provide the metalated pyridine of Formula 21.0, followed by the subsequent addition of a ketone of Formula 10.0 to provide a compound of Formula 22.0. Alternatively, a compound of Formula 22.0 can be made by treating a compound of Formula 23.0 or 23.1 with the appropriate metalated aryl ring compound of Formula 16.0 or 16.1, respectively. These reactions are usually conducted in a dry aprotic solvent such as tetrahydrofuran or diethyl ether at temperatures typically ranging from about 0° C. to reflux, depending on the solvent used.

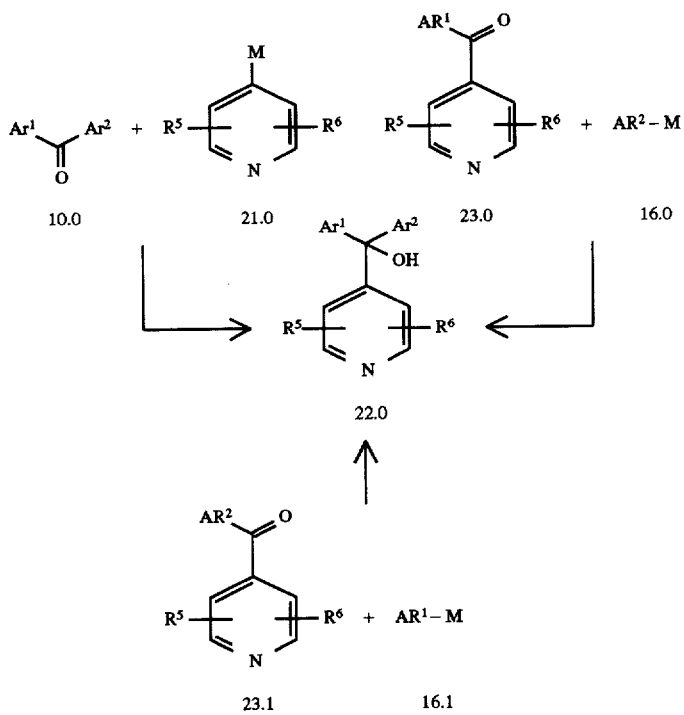

A compound of Formula 22.0 is then hydrogenated under acidic conditions in a Parr hydrogenator to effect reduction of the pyridine ring to provide a compound of Formula 2.0. The reaction is usually conducted in an acidic solvent such as glacial acetic acid or acidic ethanol in the presence of a catalyst such as platinum. The preparation of compounds of Formula 2.0 by this method is limited to cases in which the reactants or products are not effected by acid or hydrogenation (e.g., no halogens are present).

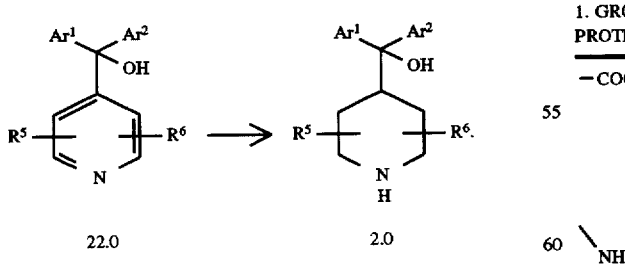

In the above processes, it is sometimes desirable and/or necessary to protect certain $R^1$, $R^2$, $R^3$, $R^4$, $R^5$, $R^6$, $R^7$, $R^8$, and/or $R^9$, groups during the reactions. Certain protecting groups are employed in the above processes but, as those skilled in the art will recognize, other protecting groups may be used in their place. Conventional protecting groups are operable as described in Greene, T. W., "Protective Groups In Organic Synthesis," John Wiley & Sons, New York, 1981. For example, the groups listed in column 1 of Table 1 below may be protected as indicated in column 2 of the table:

TABLE 1

PROTECTED GROUPS

| 1. GROUP TO BE PROTECTED | 2. PROTECTED GROUP |
|---|---|
| —COOH | —COOalkyl, —COObenzyl, —COOphenyl, —C(O—)(O—)CH3 |
| \NH/ | \NCOalkyl/, \NCObenzyl/, \NCOphenyl/ |

TABLE 1-continued

PROTECTED GROUPS

| 1. GROUP TO BE PROTECTED | 2. PROTECTED GROUP |
|---|---|
| >CO |  |
| —OH | 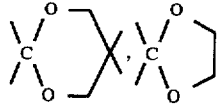, —OCH₂phenyl,<br>—OCH₃, OSi(CH₃)₂(t-Bu), |
| —NHR, wherein R is any substituent on an amino group within the scope of the claims | 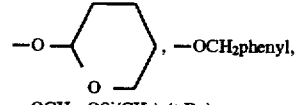,<br>—NR—CO—CF₃, —NRCOCH₃,<br>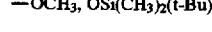 |
| —NH₂ | ,<br>—NH—C(O)—O(t-Bu) |

Other protecting groups well known in the art can also be used. After the reaction or reactions, the protecting groups may be removed by standard procedures.

The compounds of the invention possess platelet-activating factor ("PAF") antagonistic properties and are believed to possess histamine antagonistic properties. They are, therefore, useful when PAF and/or histamine are factors in the disease or disorder. This includes allergic diseases such as asthma, allergic rhinitis, adult respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), eosinophil chemotaxis, vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. In Vitro Studies—Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 mL) was collected from healthy male donors in an anticoagulant solution (5 mL) containing sodium citrate (3.8%) and dextrose (2%). Blood was centrifuged at 110×g for 15 min. and the supernatant platelet-rich plasma (PRP) carefully transferred into a polypropylene tube. Platelet-poor-plasma (PPP) was prepared by centrifuging PRP at 12,000×g for 2 min. PRP was used within 3 hr. of drawing the blood.

PAF was dissolved in chloroform:methanol (1:1, v/v) at a concentration of 2 mg/mL and stored at -70° C. An aliquot of this solution was transferred to a polypropylene tube and added under a flow of nitrogen gas. To the dried sample was added Hepes-saline-BSA (BSA=bovine serum albumen) buffer (25 mM Hepes, pH 7.4, 1254 mM NaCl, 0.7 mM MgCl₂ and 0.1% BSA) to obtain a 1 mM solution. The solution was sonicated for 5 min. This stock solution was further diluted to appropriate concentrations in Hepes-saline-BSA buffer. Collagen and adenosine diphosphate (ADP) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer. PRP (0.45 ml) in aggregometer cuvettes was continually stirred (37° C.). Solutions (50 µL) of test compounds or vehicle were added to the PRP and, after incubation for 2 min., 10–15 µL aliquots of PAF solution were added to achieve a final concentration of $1-5\times10^{-8}M$. In different experiments the aggregatory response was kept within a set limit by varying the concentration of PAF. Incubations were continued until the increase in light transmission reached a maximum (usually 2 min.). This increase in light transmission reflecting platelet aggregation is transmitted to a computer. The computer calculates the slope of transmission change, thus providing the rate of aggregation. Values for inhibition were calculated by comparing rates of aggregation obtained in the absence and the presence of the compound. For each experiment, a standard PAF antagonist such as 8-chloro-6, 11-dihydro-11-(1-acetyl-4-piperidylidene)-5H-benzo[5,6] cyclohepta[1,2-b]pyridine was used as a positive control.

Compounds that inhibit PAF-induced aggregation were tested against several other aggregating agents including collagen (0.2 mg/ml) and ADP (2 µM). Compounds showing no activity against these latter agents were considered to be specific PAF antagonists. Results are shown in TABLE 2 below.

In Vivo Studies: Agonist-Induced Responses—
Spasmogen-Induced Bronchospasm in Guinea Pigs Male Hartley guinea pigs (450–550 g) were obtained from Charles River Breeding Laboratories. The animals were fasted overnight and the following day were anesthetized with 0.9 mL/kg i.p. of dilaurethane (containing 0.1 g/mL diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 mL. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg) or PAF (0.4 µg/kg in isotonic saline containing 0.25% BSA). Each animal was challenged with only a single spasmogen. The effect of a compound on the bronchospasm is expressed as a percent inhibition of the increase in inflation pressure compared to the, increase in a control group. Results are shown in TABLE 2A below for representative examples of compounds of the present invention.

TABLE 2

INHIBITION OF PLATELET AGGREGATION INDUCED BY PAF (in vitro)

| TEST COMPOUND | INHIBITION (%) | CONCENTRATION (μM) |
|---|---|---|
| 1.0A10 | 86 | 50 |
|  | 92 | 5 |
|  | 88 | 0.5 |
|  | 67 | 0.25 |
|  | 52 | 0.125 |
| 1.0A12 | 100 | 50 |
|  | 98 | 5 |
|  | 58 | 0.5 |
|  | 47 | 0.25 |
| 1.0A8 | 89 | 50 |
|  | 100 | 5 |
|  | 74 | 0.5 |
|  | 55 | 2.5 |
|  | 26 | 1.25 |
| 1.0A11 | 83 | 50 |
|  | 76 | 5 |
|  | 7 | 0.5 |
| 1.0A9 | 100 | 50 |
|  | 24 | 5 |
| 1.0A3 | 92 | 50 |
|  | 95 | 5 |
|  | 88 | 0.5 |
|  | 69 | 0.25 |
|  | 53 | 0.125 |
|  | 41 | 0.063 |
| 1.0A5 | 91 | 2.5 |
|  | 81 | 1.2 |
|  | 59 | 0.5 |
|  | 41 | 0.25 |
|  | 35 | 0.12 |
| 1.0A1 | 97 | 0.5 |
|  | 68 | 0.25 |
|  | 28 | 0.12 |

Compound A and Compound B having the formulas, respectively,

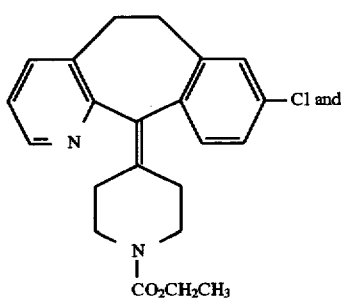

(A)

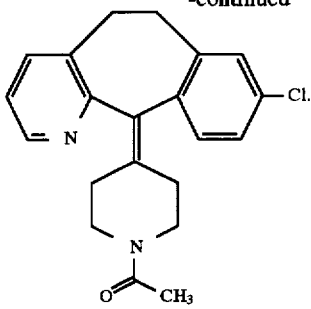

(B)

represent known compounds. For purposes of comparison, the PAF antagonism (in vitro) IC$_{50}$ (μM) for Compound A is >50, and for Compound B is 0.61.

TABLE 2A

| CMPD NO | Agonist Bronchospasm (in Vivo)-oral | | | |
|---|---|---|---|---|
|  | PAF | | Histamine | |
|  | Dose | % Inhibition | Dose | % Inhibition |
| A | 10 mg/kg | <50 | 1 mg/kg | >50 |
| B | 3 mg/kg | 4 | 3 mg/kg | 48 |
| 1.0A10 | 3 mg/kg | 93 | 10 mg/kg | 12 |
| 1.0A3 | 3 mg/kg | 87 | — | — |
| 1.0A5 | 3 mg/kg | 20 | — | — |
| 1.0A1 | 3 mg/kg | 93 | — | — |
| 1.0A8 | 3 mg/kg | 0 | — | — |
| * | 1 mg/kg | 4 | — | — |
| ** | 1 mg/kg | 94 | — | — |

*(+)-enantiomer of 1.0A10 (i.e., 1.0A13 or 1.0A14)
**(−)-enantiomer of 1.0A10 (i.e., 1.0A13 or 1.0A14)

Comparative data demonstrating the longer duration of the compounds of this invention are given in TABLE 3 below. In TABLE 3, Compounds C and D represent known compounds having the formulas:

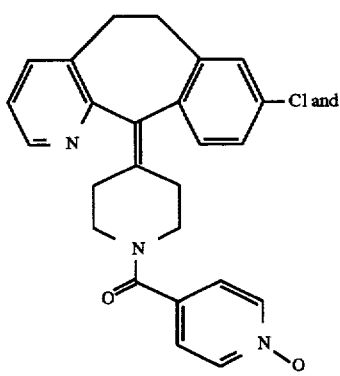

(C)

and

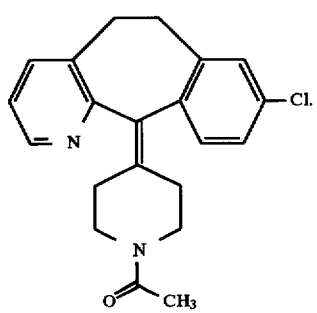

(D)

Compound C is,disclosed in WO90/13548 (PCT/US90/02251), and Compound D is disclosed in U.S. Pat. No. 4,826,853.

TABLE 3

| | Agonist Bronchospasm (in Vivo) - Oral PAF | | |
|---|---|---|---|
| Compound | Dose | % Inhibition | Time |
| C | 5 mg/kg | 37 | 4 |
| | 5 mg/kg | 12 | 8 |
| D | 15 mg/kg | 61 | 4 |
| | 15 mg/kg | 32 | 8 |
| 1.0A10 | 4 mg/kg | 99 | 6 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example there may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as is conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application. The appropriate dosage can be determined by comparing the activity of the compound with the activity of a known PAF and histamine antagonist such as 8-chloro-6,11-dihydro-11-(1-acetyl-4-piperidylidene)-5H-benzo[5,6]cyclohepta[1,2-b]pryidine, which compound is disclosed in U.S. Pat. No. 4,826,853.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day preferably 10 to 750 mg/day, in two to four divided doses to achieve relief of the symptoms. The compounds are non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

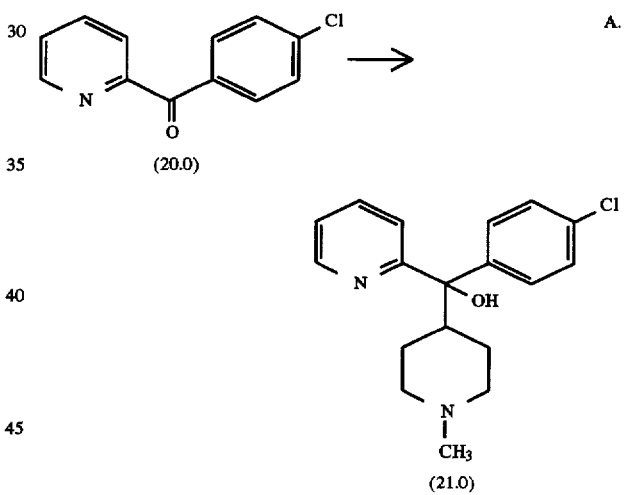

To a mixture of 6.0 g (27.6 mmol) of a compound of Formula 20.0 in 150 mL of dry tetrahydrofuran at 0° C. and under an atmosphere of nitrogen was added dropwise 44 mL of 1.25 M (55 mmol) of the Grignard reagent prepared from N-methyl-4-chloropiperidine. The reaction mixture was then allowed to slowly warm to room temperature and stir overnight. The next day another 22 mL (27.5 mmol) of the Grignard reagent was added, and the mixture was stirred for another 30 minutes. The reaction mixture was quenched with a 10% aqueous solution of ammonium chloride and then extracted three times with ethyl acetate. The organic portions were combined, washed with brine, dried over sodium sulfate, filtered, and concentrated in vacuo to render 8.8 gms of the crude product. The residue was purified by flash chromatography [10% methanol in methylene chloride] to provide 1.1 g (13%) of the compound of Formula 21.0 as a glass.

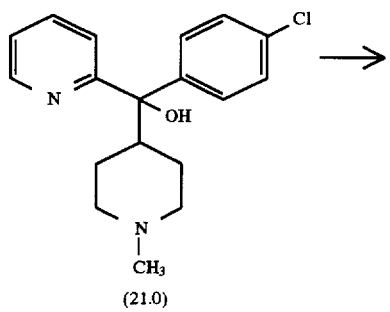
(21.0)

B.

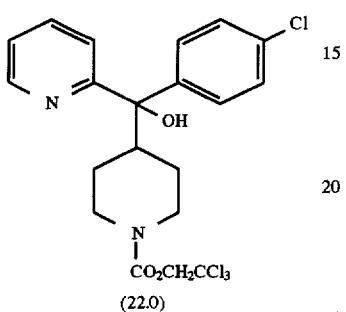
(22.0)

To a mixture of 1.1 g (3.47 mmol) of the compound of Formula 21.0 and 3.6 mL of triethylamine in 30 mL of dry toluene at 90° C. and under a nitrogen atmosphere was added dropwise 1.1 mL (26.1 mmol) of 2,2,2-trichloroethyl chloroformate. After 5 hours the mixture was diluted with methylene chloride and washed with a saturated solution of sodium carbonate and then brine. The organic portion was dried over sodium sulfate, filtered, and concentrated in vacuo. The residue was purified via flash chromatography [20% ethyl acetate in hexane] to afford 1.28 g (77%) of the compound of Formula 22.0 as a glass.

C.
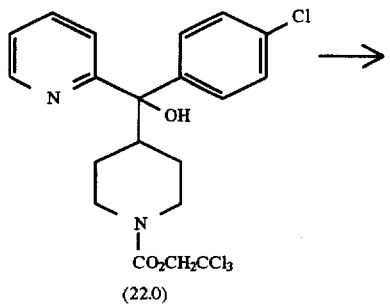
(22.0)

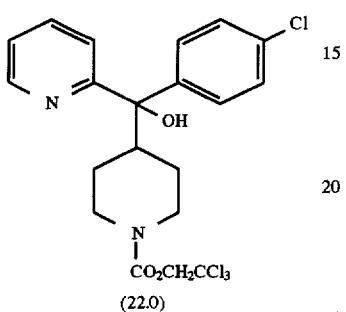
(23.0)

To a mixture of 1.28 (2.68 mmole) of the compound of Formula 22.0 in 30 mL of glacial acetic acid was added 1.3 g (19.9 mmol) of zinc dust. After 90 minutes the mixture was filtered, basified with 5% aqueous sodium hydroxide, and extracted three times with methylene chloride. The combined organic portions were washed once with brine, dried over sodium sulfate, filtered, and concentrated in vacuo to yield 798 mg (98%) of the compound of Formula 23.0 as a glass.

PREPARATIVE EXAMPLE 2

By employing basically the same procedure as set forth in PREPARATIVE EXAMPLE 1 above, but substituting the starting ketones of column 1 in TABLE 4 below for the compound of Formula 20.0, the compounds listed in column 2 of TABLE 4 were prepared.

TABLE 4

| STARTING KETONE | PRODUCT |
|---|---|
| (24.0) | (25.0) |

TABLE 4-continued
| STARTING KETONE | PRODUCT |
|---|---|
| 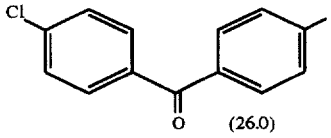 (26.0) | 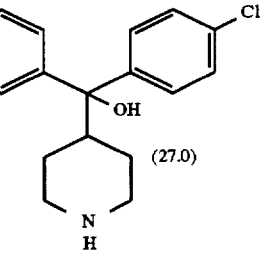 (27.0) |
| 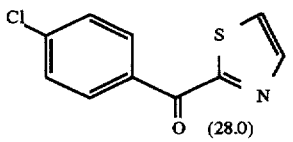 (28.0) | 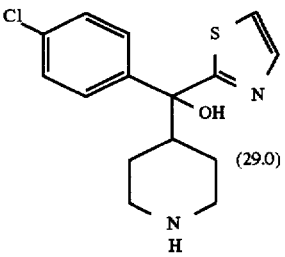 (29.0) |
| 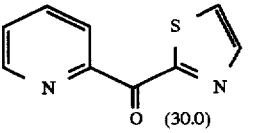 (30.0) | 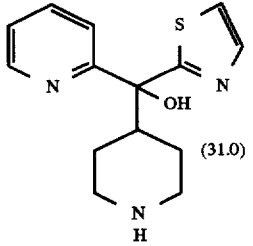 (31.0) |
| 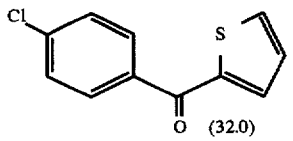 (32.0) | 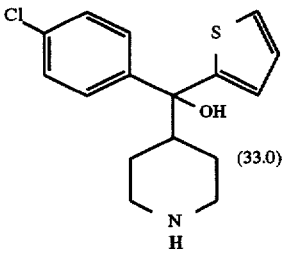 (33.0) |
PREPARATIVE EXAMPLE 3
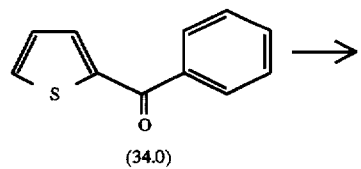
(34.0)
A.
-continued
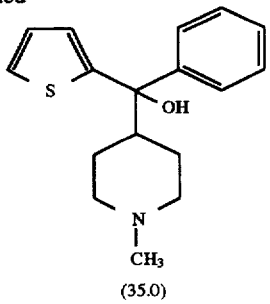
(35.0)

To a mixture of the Grignard reagent prepared from 490 g (3.67 mol) of 1-methyl-4-chloropiperidine in 7000 mL of THF at 0° C. was slowly added a solution of 376 g (2.00 mol) of the compound of Formula 34.0 in 1200 mL of dry tetrahydrofuran. The mixture was then refluxed overnight. The mixture was partially concentrated and the residue cooled to 0° C., slowly quenched with 2000 mL of saturated aqueous ammonium chloride, and extracted with chloroform. The organic portion was washed with water, dried over sodium sulfate, filtered, and concentrated in vacuo to yield the crude product. The crude product was then triturated with petroleum ether and the resultant solid recrystallized from acetonitrile to yield 284 g (49%) of the compound of Formula 35.0 as a tan solid: MP 141°–144° C.

B. (35.0)

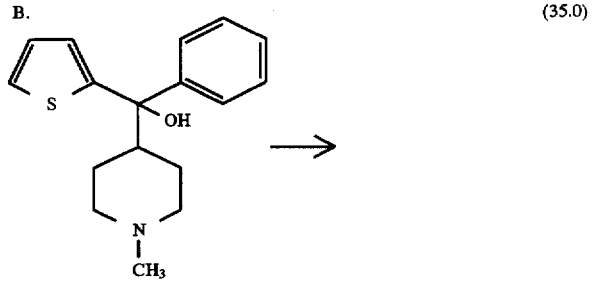

To a mixture of 63.0 g (0.219 mol) of the compound of Formula 35.0 in 500 mL of dry carbon tetrachloride was slowly added with gentle warming 81.4 g (0.750 mole) of ethyl chloroformate. The mixture was then refluxed overnight, after which it was cooled and poured into water. The organic portion was isolated, and the aqueous layer was extracted with chloroform. The combined organic portions were washed with water, dried over sodium sulfate, filtered, and concentrated in vacuo to yield a brown oil. The crude product was triturated with hexane and the resultant solid recrystallized from acetonitrile to yield 30.0 g (42%) of the compound of Formula 36.0 as a solid: MP 92°–95° C.

C. (36.0)

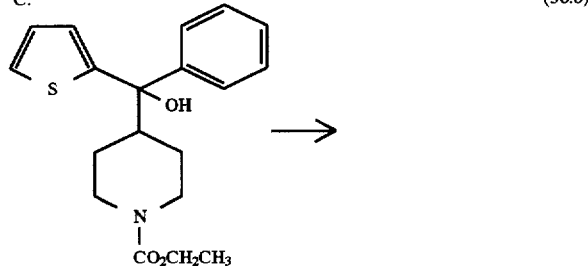

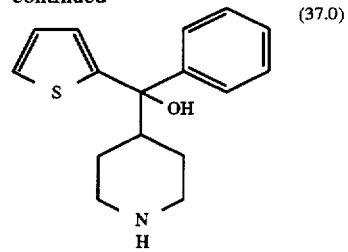

(37.0)

A mixture of 59.0 g (0:179 mol) of the compound of Formula 36.0 and 60.0 g (1.07 mole) of potassium hydroxide in 1500 mL of propanol was refluxed overnight. The mixture was concentrated in vacuo and the residue was taken up in water and extracted with ether. The organic portion was isolated, washed with water, dried over sodium sulfate, filtered, and concentrated in vacuo to yield a residue, which was triturated with hexane and subsequently recrystallized from ethyl acetate to provide 33.0 g (67%) of the compound of Formula 37.0 as a white solid: MP 169°–171° C.

PREPARATIVE EXAMPLE 4

A. (38.0)

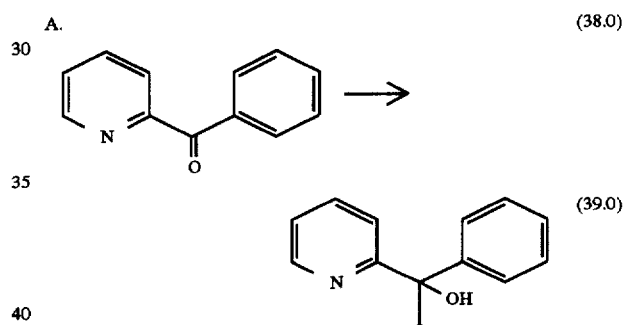

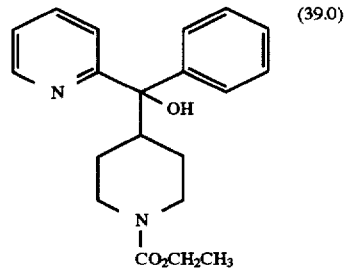

Under anhydrous conditions, sodium metal (20.2 g, 0.879 mol) was dissolved in 1500 mL of dry liquid ammonia. After 30 minutes a solution of 73.2 g (0.400 mol) of the compound of Formula 38.0 in 300 mL of dry tetrahydrofuran was slowly added, followed by, after another 30 minutes, a solution of 92.0 g (0.480 mol) of N-ethyloxycarbonyloxy-4-chloropiperidine in an equal volume of dry tetrahydrofuran. After 2 hours 100 g of ammonium chloride was added, and the reaction mixture was then allowed to stir overnight in order to allow the ammonia to evaporate. Following the addition of water, the mixture was extracted with chloroform. The isolated organic portion was washed with water, dried over Sodium sulfate, filtered, and concentrated in vacuo to yield a dark brown oil. The residue was triturated with petroleum ether to provide a tan solid which was subsequently recrystallized from ethanol to provide 100 g (74%) of the compound of Formula 39.0 as a solid: MP 125°–128° C.

B. (39.0)

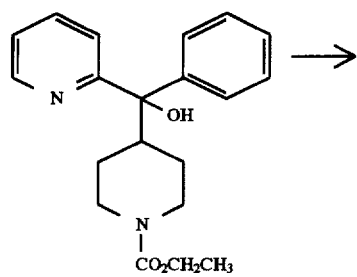

(40.0)

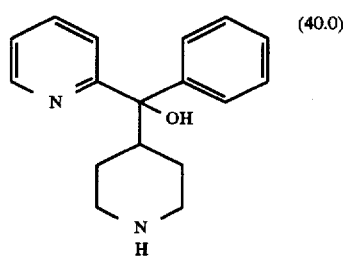

A mixture of 100 gms (0.294 mmol) of the compound of Formula 39.0 in 3000 mL of concentrated hydrochloric acid was refluxed overnight. The mixture was concentrated to a smaller volume, slowly basified with cooling with 50% aqueous sodium hydroxide, and extracted with chloroform. The organic portion was washed once with water, dried over sodium sulfate, filtered, and concentrated in vacuo to yield a brown oil. The residue was triturated with hexane to provide a solid which was subsequently recrystallized from ethyl acetate to provide 62 g (79%) of the compound of Formula 40.0 as a solid: MP 127°–129° C.

PREPARATIVE EXAMPLE 5

A. (41.0)

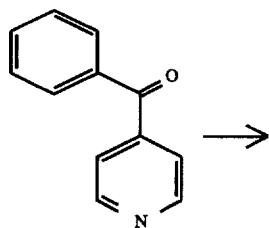

(42.0)

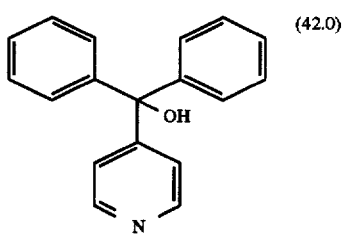

A mixture of 40.0 gms (1.65 mmole) of magnesium turnings, a few drops of bromobenzene, and a few crystals of iodine in 1000 mL of dry ethyl ether was heated to initiate reaction. Immediately, a solution of 260 gms. (1.65 mole) of bromobenzene in an equal volume of dry ethyl ether was added at such a rate to maintain a gentle reflux. After the addition was complete, the mixture was heated until all the magnesium dissolved, and then the mixture was cooled to 0° C. A solution of 200 g (1.09 mole) of the compound of Formula 41.0 in 2500 mL of dry ethyl ether was slowly added over a period of 1.5 hours. The mixture was allowed to warm to room temperature and then refluxed for 3 hours. It was cooled back down to 0° C. and 1000 mL of a saturated aqueous solution of ammonium chloride was slowly added. The white precipitate was filtered off and washed successively with 1000 mL of cold water, 1000 mL of brine, and 2000 mL of ethyl ether. The product was recrystallized from acetic acid and water to provide 215 g (75%) of the compound of Formula 42.0 as a solid: MP 235°–238° C.

B. (42.0)

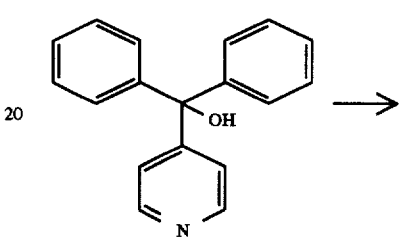

(43.0)

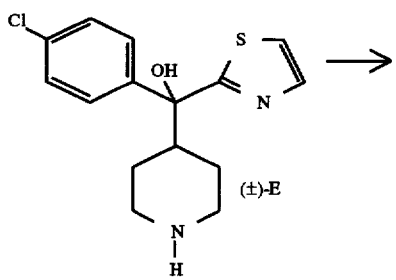

A mixture of 104.4 gms (0.400 mmol) of the compound of Formula 42.0 and 15.0 g of platinum oxide in 1500 mL of glacial acetic acid was shaken in a Parr hydrogenator at an initial pressure of 60 psi for 4 hours. The reaction mixture was filtered, and the filtrate concentrated in vacuo to yield a white solid, which was suspended in water. The solution was basified with a 50% aqueous solution of sodium hydroxide and extracted with chloroform. The organic portion was washed with water, dried over sodium sulfate, filtered, and concentrated again in vacuo. The residue was recrystallized from ethanol to yield 85 g (79%) of the compound of Formula 43.0 as a white solid: MP 156°–159° C.

PREPARATIVE EXAMPLE 6

-continued

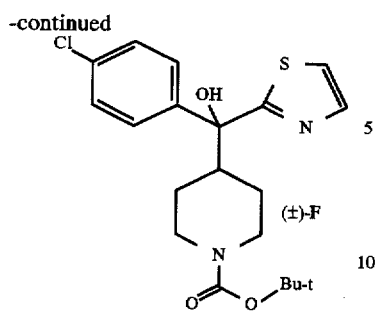

(±)-F

PREPARATIVE EXAMPLE 8

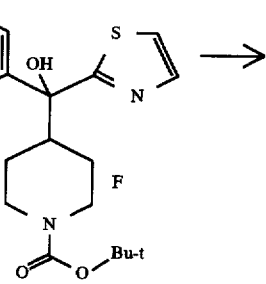

With a bath of ice and dry ice, a solution of the racemic amine E (5.03 g, 16.3 mmol) in dry dichloromethane (100 mL) was cooled to 0° C., and a solution of di-t-butyl carbonate (4.00 g, 18.3 mmol) in dry dichloromethane was added. The resulting reaction mixture was stirred for 3 hours at 0° C. in an atmosphere of nitrogen. The mixture was stirred for a further 12 to 18 hrs at 25° C., and then it was poured into a solution of sodium dihydrogen phosphate (500 mL, 10% (weight/volume)). The aqueous and organic layers were separated, and the aqueous layer was extracted with dichloromethane (three five-mL portions), and all the dichloromethane solutions were combined. The organic solution was washed with 1M sodium bicarbonate solution and with water, and then the organic solution was added, filtered and concentrated to give a crude sample of the desired carbamate F.

The crude product was chromatographed over silica gel, and the desired product F was eluted with methanol-dichloromethane (0.3:97.7, by volume). The progress of the separation was monitored by thin-layer chromatography and the appropriate fractions were combined. These fractions were evaporated, and the residue was crystallized from carbon tetrachloride-pet. eth. to give pure, racemic t-butylcarbamate F, m. p. 93°–98° C.

PREPARATIVE EXAMPLE 7

High-Pressure Liquid Chromatographic Resolution of Enantiomers

Racemic t-butylcarbamate (±)-F (5.9 g in portions of about 300 mg each) was chromatographed over a preparative, cellulose carbamate-silica gel column (Chiralcel OD, 50 mm in inside diameter and 500 mm in length). The enantiomers were eluted with hexane-ethanol-diethylamine (98:2:1) at a 40-mL per minute flow rate, and the resolution was monitored with an ultraviolet detector operating at 254 nm. The appropriate fractions were combined and concentrated, and the residues were crystallized from diethyl ether to give the separate enantiomers as follows: (+)-F, m.p. 139°–142° C., retention time ($R_t$) 13 min, $[\alpha]_D^{22.5°}$ +7.3° (4.9 mg in 2 mL of CHCl$_3$); and (−)-F, m.p. 140°–142° C., $R_t$ 10.6 min, $[\alpha]_D^{22.5°}$ −8.8° (4.4 mg in 2 mL of CHCl$_3$).

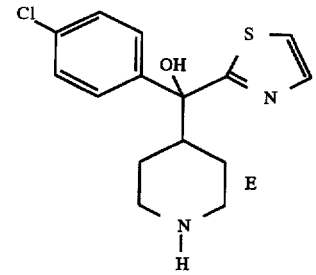

E

Iodotrimethylsilane (0.025 mL) was added to a solution of the t-butyl carbamate (±)-F (60 mg, 146 mmol) in dry acetonitrile (3 mL) containing suspended potassium carbonate (0.12 g), and the mixture was stirred for 2 hours in an atmosphere of nitrogen and at 25° C. Methanol (5 mL) was added, and the resulting mixture was filtered and concentrated to give the desired amine (±)-E.

By a similar procedure, the enantiomers of amine E were separately prepared.

EXAMPLE 1

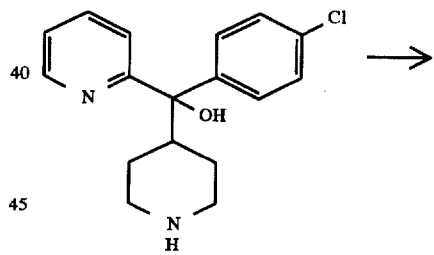

(23.0)

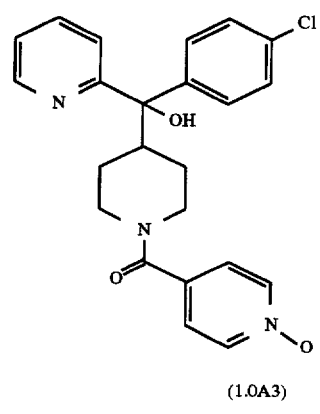

(1.0A3)

To a mixture of 320 mg (1.06 mmol) of the compound of Formula 23.0 (Preparative Example 1 ) and 181 mg (1.30 mmol) of isonicotinic acid N-oxide in 30 mL of dry methylene chloride at 0° C. and under an atmosphere of nitrogen was added 327 mg (1.71 mmol) of DEC and 170 mg (1.58 mmol) of HOBT. After 2.5 hours the reaction was poured into methylene chloride, and washed once with an aqueous solution of 0.5M sodium bicarbonate and once with brine. The organic portion was added over sodium sulfate, filtered, and concentrated in vacuo. The residue was purified by flash chromatography [5% methanol in methylene chloride] to yield 400 mg (89%) of the compound of Formula 1.0A3 as a white glass: MS (FAB) m/z 424 (M$^+$+1).

EXAMPLE 2

By employing basically the same procedure as set forth in EXAMPLE 1 above, but substituting the starting compounds of column 1 in TABLE 5 below for the compound of Formula 23.0 the compounds listed in column 2 of TABLE 5 were prepared. The physical data for these compounds of the invention are listed in column 3 of the table.

TABLE 5

| STARTING COMPOUND | COMPOUND OF THE INVENTION | PHYSICAL DATA |
|---|---|---|
| (37.0) | (1.0A4) | white crystals MP: 238–240° C.; MS (FAB) m/z 395 (M$^+$ + 1) |
| (29.0) | (1.0A10) | m. p. 199–205° C. (from CH$_2$Cl$_2$) |
| (31.0) | (1.0A12) | m. p. 207–210° C. (from CH$_3$CN) |

TABLE 5-continued

| STARTING COMPOUND | COMPOUND OF THE INVENTION | PHYSICAL DATA |
|---|---|---|
| 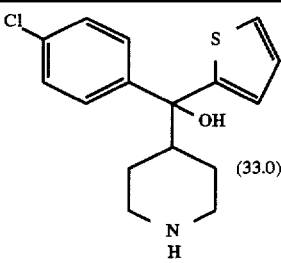 (33.0) | 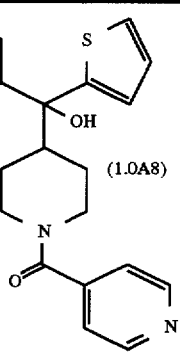 (1.0A8) | MS (FAB) m/z 429 ([M + 1]+) |

By a similar procedure using the separate enantiomers of amine E (see Preparative Examples 6 to 8), the separate enantiomers of Formula 1.0A10, specifically 1.0A13 and 1.0A14, are prepared:

(+)-α-(4-chlorophenyl)-1-(4-pyridinylcarbonyl)-α-(2-thiazolyl)-4-piperidinemethanol $N^1$-oxide. m.p. 215°–217° C. (from ethanol-diethyl ether), $[\alpha]_D^{22.5°}$ + 20.6° (c=0.150 g/ml, MeOH); and (−)-α-(4-chlorophenyl)-1-(4-pyridinylcarbonyl)-α-(2-thiazolyl)-4-piperidinemethanol $N^1$-oxide. m.p. 214°–216° C. (from acetonitrile-diethyl ether), $[\alpha]_D^{22.5°}$ −17.8° (c=0.161 g/ml, MeOH).

EXAMPLE 3

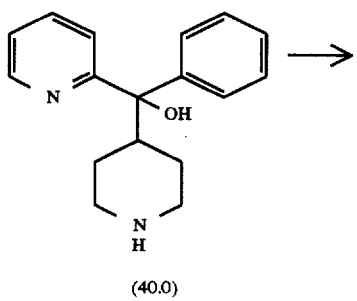
(40.0)

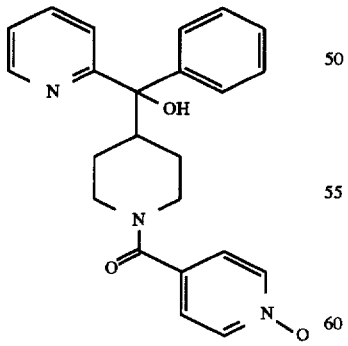
(1.0A2)

To a mixture of 4.491 g (16.7 mmol) of the compound of Formula 40.0 (Preparative Example 4), 2.524 g (18.1 mmol) of isonicotinic acid N-oxide, and 2.382 g (17.6 mmol) of HOBT in 150 mL of dry methylene chloride at −10° C. and under an atmosphere of nitrogen, was added dropwise over 15 minutes a solution of 3.788 g (19.8 mmol) of DEC in 60 mL of methylene chloride. The mixture was then slowly allowed to warm to room temperature. After 3.5 hours the reaction mixture was taken up in additional methylene chloride and washed twice with 10% aqueous sodium dihydrogen phosphate (w/v), once with a 1.0N aqueous solution of sodium hydroxide, and once with water. The organic portion was dried over magnesium sulfate, filtered, and concentrated in vacuo. The residue was recrystallized from hot methylene chloride to afford 4.51 g (69%) of the compound of Formula 1.0A2 as a white solid: MS (FAB) m/z 390 (M⁺+1).

EXAMPLE 4

By employing basically the same procedure as set forth in EXAMPLE 3 above, but substituting the starting compounds of column 1 in TABLE 6 below for the compound of Formula 40.0, the compounds listed in column 2 of TABLE 6 were prepared. The physical data for these compounds of the invention are listed in column 3 of the table.

TABLE 6
| STARTING COMPOUND | COMPOUND OF THE INVENTION | PHYSICAL DATA |
|---|---|---|
| (25.0) | (1.0A1) | tan solid MP: 193–195°C.; MS(FAB) m/z 391(M⁺ + 1) |
| (27.0) | (1.0A6) | tan solid MP: 240° C. (dec); MS (FAB) m/z 457 (M⁺ + 1) |
| (43.0) | (1.0A7) | white solid MP: 268–269° C.; MS (FAB) m/z 389 (M⁺ + 1) |
EXAMPLE 5
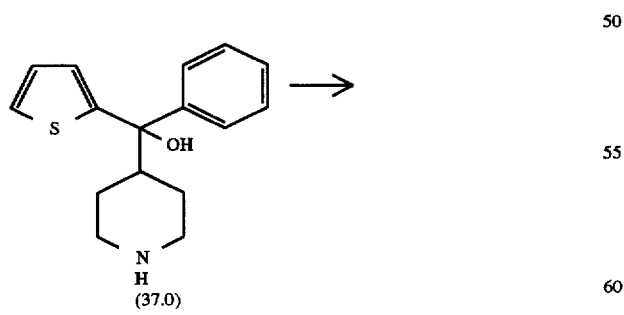
-continued
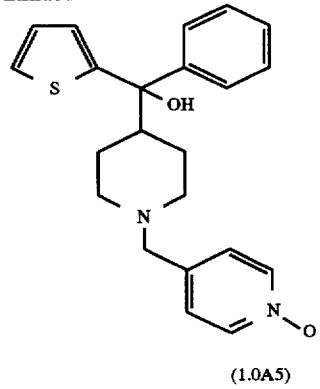

Triphenyl phosphine (814 mg, 3.10 mmol) was added to a mixture containing 384 mg (3.07 mmol) of 4-pyridylcarbinol N-oxide and 1.03 g (3.11 mmol) of carbon tetrabromide in 30 mL of dry methylene chloride at room temperature and under an atmosphere of nitrogen. After 1 hour, 500 mg (1.83 mmol) of the compound of Formula 37.0 (Preparative Example 3) was added followed by 433 μL (3.11 mmol) of triethylamine. After another 1.5 hours, the mixture was taken up in methylene chloride and washed with a solution of 0.5N aqueous sodium carbonate and brine. The organic phase was dried over sodium sulfate, filtered, and concentrated in vacuo to yield a residue, which was purified by flash chromatography [8% methanol in methylene chloride]. The purified product was triturated with isopropyl ether and pentane to provide 180 mg (26%) of the compound of Formula 1.0A5 as a tan solid: MP: 193°–196° C.; MS (FAB) m/z 381 (M⁺+1).

EXAMPLE 6

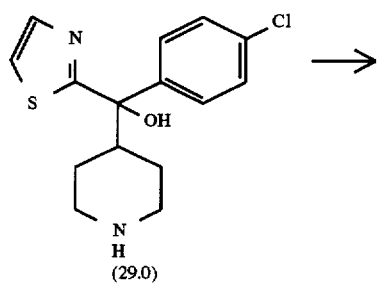

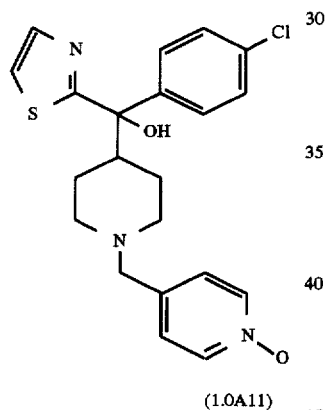

(1.0A11)

The compound of Formula 29.0 (0.5 g) was added to a solution of 4-(chloromethyl)-pyridine-N-oxide hydrochloride (0.4 g) dissolved in methanol (5 mL) containing triethylamine (0.38 g) and cooled at 0° to 10° C. The mixture was then allowed to stir 3 hrs. at 25° C., and was afterward diluted with a little ethyl acetate. The solution was basified (pH 12) with concentrated aqueous ammonia, and was extracted with dichloromethane. Combined extracts were dried (MgSO₄), filtered, and concentrated. The residue was chromatographed over silica gel, and dichloromethane-methanol-concentrated aqueous ammonia (96:3.6:0.4, by volume) eluted the compound of Formula 1.0A11 m.p. 201°–208° C. from CH₂Cl₂.

4-(chloromethyl)-pyridine-N-oxide hydrochloride was prepared as follows: Thionyl chloride (6.4 mL) was added slowly and with vigorous stirring to 4-pyridylcarbinol-N-oxide (10 g). The solid dissolved, and the reaction mixture became warm, and evolved a gas, and solidified. The cooled solid was collected on a filter, washed with hexanes, and dried at 40° C. under vacuum to give 4-(chloromethyl)-pyridine-N-oxide hydrochloride.

EXAMPLE 7

By employing basically the same procedure as set forth in EXAMPLE 6 above, but substituting the compound of Formula 33.0:

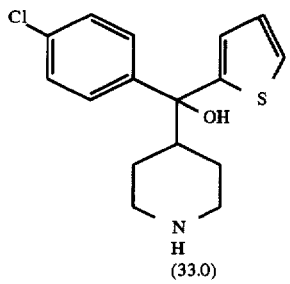

for the starting compound instead of the compound of Formula 29.0, the compound the compound of Formula 1.0A9 was prepared:

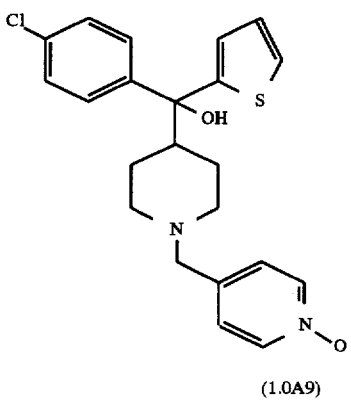

Physical data for the compound of Formula 1.0A9 were: FAB-MS m/z 415 ([M+1]⁺.

The following are examples of pharmaceutical dosage forms which contain a compound of the invention. As used therein, the term "active compound" is used to designate the compound

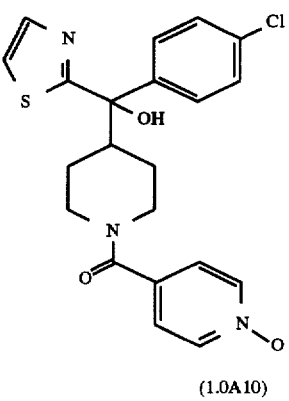

The scope of the invention in its pharmaceutical composition aspect is not to be limited by the examples provided, since any other compound of Formula 1.0 can be substituted into the pharmaceutical composition examples.

Pharmaceutical Dosage Form Examples

EXAMPLE A

Tablets

| No. | Ingredients | mg/tablet | mg/tablet |
| --- | --- | --- | --- |
| 1. | Active compound | 100 | 500 |
| 2. | Lactos USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
| --- | --- | --- | --- |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of treating inflammation or allergy comprising administering to a mammal in need of such treatment an antiinflammatory or anti-allergic effective amount of a compound of Formula 1.0

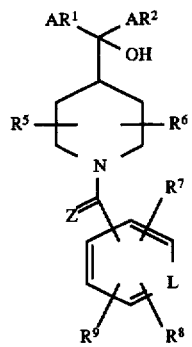

(1.0)

or a pharmaceutically acceptable salt or solvate thereof, wherein:

$AR^1$ represents

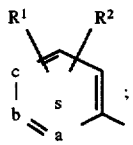

$AR^2$ represents

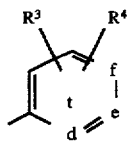

or a five-membered heterocyclic aromatic group selected from the group consisting of Formulas I to XII:

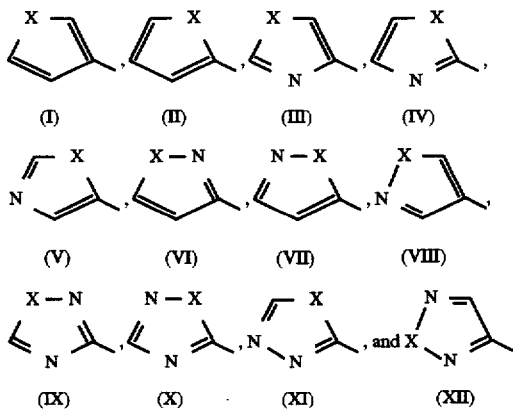

wherein X represents O, S, or $NR^{10}$ wherein $R^{10}$ is as defined below, said five-membered heterocyclic aromatic group can optionally be substituted with a group $R^1$ as defined below;

one of a, b and c represents N or $N^+O^-$ and the remaining a, b, and c represent C, or all of a, b and c represent C;

one of d, e and f represents N or $N^+O^-$ and the remaining d, e, and f represent C, or all of d, e and f represents C;

L represents $N^+O^-$;

$R^1$, $R^2$, $R^3$, and $R^4$ are each independently selected from the group consisting of: H, halo, —$CF_3$, —$OR^{11}$, —$C(O)R^{11}$, $SR^{11}$, —$S(O)_qR^{12}$ wherein q is 1 or 2, —$N(R^{11})_2$, —$NO_2$, —$OC(O)R^{11}$, —$CO_2R^{11}$, —OCO$_2$R$^{12}$, —CON(R$^{11}$)$_2$, —NR$^{11}$C(=O)R$^{11}$, —CN, alkyl, aryl, alkenyl and alkynyl, said alkyl group is optionally substituted with —OR$^{11}$, —SR$^{11}$, —N(R$^{11}$)$_2$ or —CO$_2$R$^{11}$, and said alkenyl group is optionally substituted with halo, —OR$^{12}$ or —CO$_2$R$_{11}$;

R$^5$ and R$^6$ are each independently selected from the group consisting of: H, alkyl and aryl; or R$^5$ can be taken together with R$^6$ to represent =O or =S;

R$^7$, R$^8$ and R$^9$ are each independently selected from the group consisting of: H, halo, —CF$_3$, —OR$^{11}$, —C(O)R$^{11}$, —SR$^{11}$, —S(O)$_e$R$^{12}$ wherein e is 1 or 2, —N(R$^{11}$)$_2$, —NO$_2$, CN, —CO$_2$R$^{11}$, —OCO$_2$R$^{12}$, —OC(O)R$^{11}$, —CON(R$^{11}$)$_2$, —NR$^{11}$C(O)R$^{11}$, alkyl, aryl, alkenyl and alkynyl, said alkyl group is optionally substituted with —OR$^{11}$, —SR$^{11}$, —N(R$^{11}$)$_2$, or —CO$_2$R$^{11}$, and said alkenyl group is optionally substituted with halo, —OR$^{12}$ or —CO$_2$R$^{11}$;

R$^{10}$ is selected from the group consisting of: H and alkyl;

R$^{11}$ is selected from the group consisting of: H, alkyl and aryl;

R$^{12}$ is selected from the group consisting of: alkyl and aryl; and

Z is selected from the group consisting of: O and S, or Z optionally represents H and R$^{10}$;

wherein said alkyl contains from one to twenty carbon atoms, said alkenyl contains from 2 to 12 carbon atoms, said alkynyl contains from 2 to 12 carbon atoms, and said aryl contains from 6 to 14 carbon atoms.

2. The method of claim 1 wherein said five membered heterocyclic aromatic group is selected from the group consisting of:

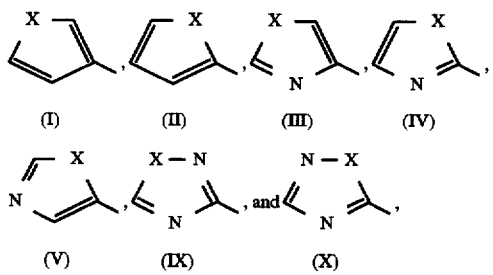

wherein X is selected from the group consisting of: O, S, and NR$^{10}$.

3. The method of claim 2 wherein said heterocyclic group is selected from the group consisting of:

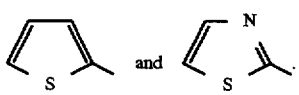

4. The method of claim 1 wherein AR$^2$ represents:

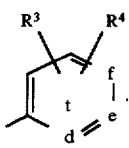

5. The method of claim 1 wherein AR$^1$ and AR$^2$ are each independently selected from the group consisting of: phenyl, halophenyl, thienyl, thiazolyl, and pyridyl.

6. The method of claim 1 wherein AR$^1$ and AR$^2$ are selected from the group of AR$^1$ and AR$^2$ combinations consisting off phenyl and phenyl; pyridyl and pyridyl; pyridyl and phenyl; thienyl and phenyl; thiazolyl and phenyl; thiazolyl and pyridyl; pyridyl and chlorophenyl: chlorophenyl and chlorophenyl; thienyl and chlorophenyl; and thiazolyl and chlorophenyl.

7. The method of claim 1 wherein R$^1$, R$^2$, R$^3$, and R$^4$ are each independently selected from the group consisting of: H, halo, —OR$^{11}$, and alkyl.

8. The method of claim 1 wherein R$^5$ and R$^6$ are each hydrogen.

9. The method of claim 1 wherein R$^7$, R$^8$, and R$^9$ are each independently selected from the group consisting of: H, halo, —OR$^{11}$, and alkyl.

10. The method of claim 1 wherein Z is O.

11. The method of claim 1 wherein b and c of AR$^1$ are C; e and f of AR$^2$ are C; R$^1$, R$^2$, R$^3$, and R$^4$ are each independently selected from the group consisting of: H, halo, —OR$^{11}$, and alkyl; R$^5$ and R$^6$ are each H; R$^7$, R$^8$, and R$^9$ are each independently selected from the group consisting of: H, halo, —OR$^{11}$, and alkyl; and; Z is O.

12. The method of claim 11 wherein R$^1$, R$^2$, R$^3$, R$^4$, R$^7$, R$^8$, and R$^9$ are selected from the group consisting of H and Cl; and AR$^1$ and AR$^2$ are each independently selected from the group consisting of: phenyl, chlorophenyl, thienyl, thiazolyl, and pyridyl.

13. The method of claim 1 wherein inflammation is treated and said compound has the Formula 1.0A:

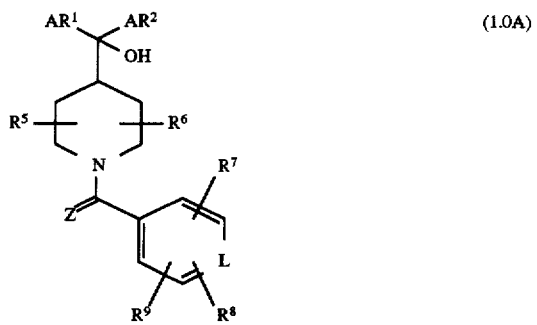

(1.0A)

wherein b and c of AR$^1$ are C; e and f of AR$^2$ are C; L represents N$^+$O$^-$; R$^1$, R$^2$, R$^3$, and R$^4$ are each independently selected from the group consisting of: H, halo, —OR$^{11}$, and alkyl; R$^5$ and R$^6$ are each H; R$^7$, R$^8$, and R$^9$ are each independently selected from the group consisting of: H, halo, —OR$^{11}$, and alkyl; and Z is O or H$_2$.

14. The method of claim 13 wherein Z is O; R$^1$, R$^2$, R$^3$, R$^4$, R$^7$, R$^8$, and R$^9$ are selected from the group consisting of H and Cl; and AR$^1$ and AR$^2$ are each independently selected from the group consisting of: phenyl, halophenyl, thienyl, thiazolyl, and pyridyl.

15. The method of claim 14 wherein AR$^1$ and AR$^2$ are selected from the group of AR$^1$ and AR$^2$ combinations consisting of: phenyl and phenyl; pyridyl and pyridyl; pyridyl and phenyl; thienyl and phenyl; thiazolyl and phenyl; thiazolyl and pyridyl; pyridyl and chlorophenyl: chlorophenyl and chlorophenyl; thienyl and chlorophenyl; and thiazolyl and chlorophenyl.

16. The method of claim 1 wherein allergy is treated and said compound has the Formula 1.0A:

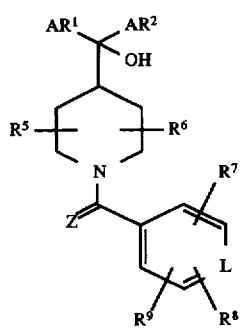 (1.0A)

wherein b and c of AR¹ are C; e and f of AR² are C; L represents $N^+O^-$; $R^1$, $R^2$, $R^3$, and $R^4$ are each independently selected from the group consisting of: H, halo, —$OR^{11}$, and alkyl; $R^5$ and $R^6$ are each H; $R^7$, $R^8$, and $R^9$ are each independently selected from the group consisting of: H, halo, —$OR^{11}$, and alkyl; and Z is O or $H_2$.

17. The method of claim 16 wherein Z is O; $R^1$, $R^2$, $R^3$, $R^4$, $R^7$, $R^8$, and $R^9$ are selected from the group consisting of H and Cl; and AR¹ and AR² are each independently selected from the group consisting of: phenyl, halophenyl, thienyl, thiazolyl, and pyridyl.

18. The method of claim 17 wherein AR¹ and AR² are selected from the group of AR¹ and AR² combinations consisting of: phenyl and phenyl; pyridyl and pyridyl; pyridyl and phenyl; thienyl and phenyl; thiazolyl and phenyl; thiazolyl and pyridyl; pyridyl and chlorophenyl; chlorophenyl and chlorophenyl; thienyl and chlorophenyl; and thiazolyl and chlorophenyl.

19. The method of claim 1 wherein said compound is selected from the group of formulas consisting of:

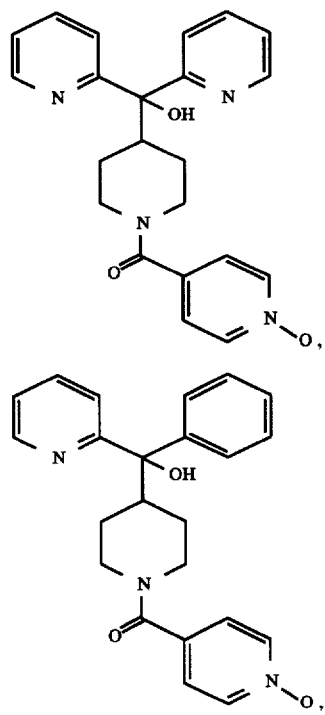

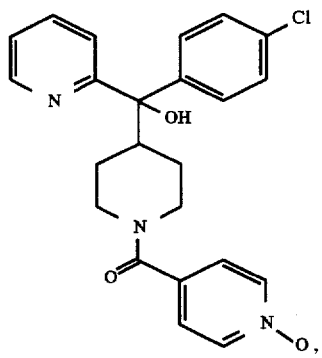 (1.0A3)

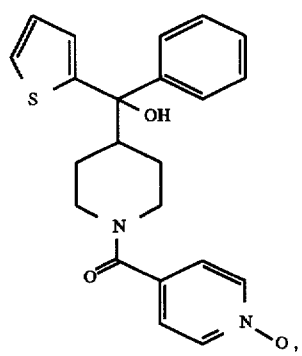 (1.0A4)

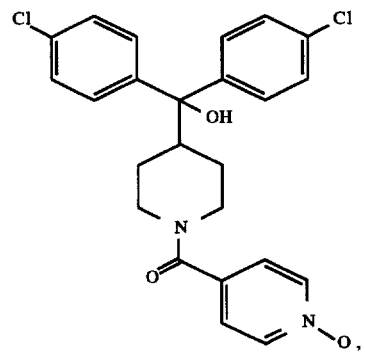 (1.0A6)

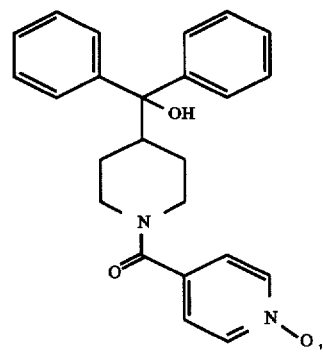 (1.0A7)

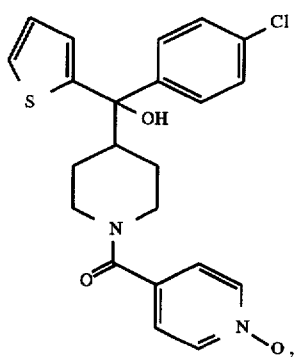
(1.0A8)
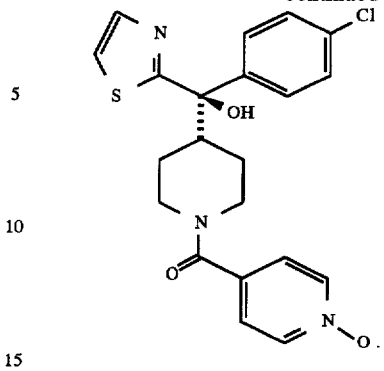
(1.0A14)
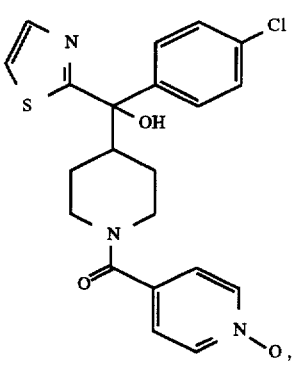
(1.0A10)
20. The method of claim 1 wherein said compound is selected from the group of formulas consisting of:
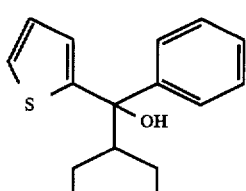
(1.0A5)
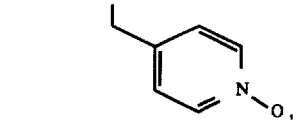
(1.0A12)
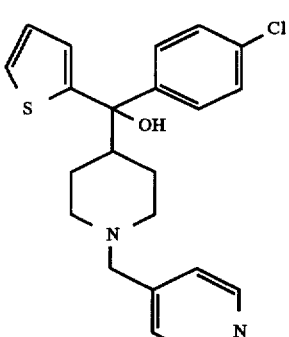
(1.0A9)
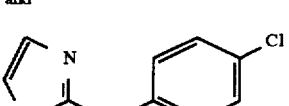
(1.0A13)
and
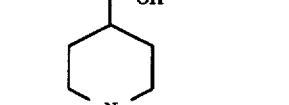
(1.0A11)
and
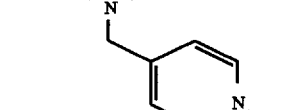

21. The method of claim 19 wherein said compound is:
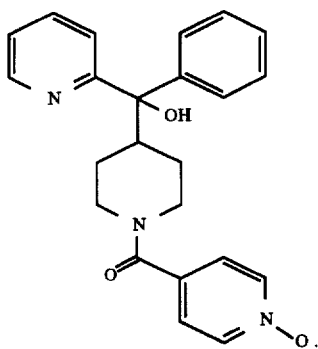
(1.0A2)
22. The method of claim 19 wherein said compound is selected from the group consisting of:
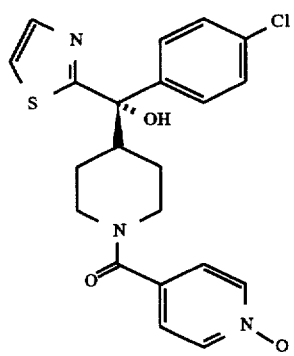
(1.0A13)
and
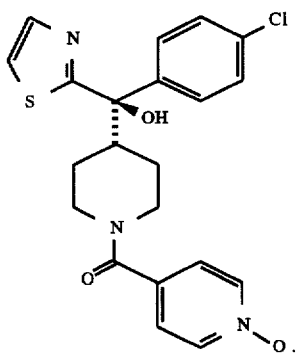
(1.0A14)
* * * * *